(12) United States Patent
Duc et al.

(10) Patent No.: US 10,820,900 B2
(45) Date of Patent: Nov. 3, 2020

(54) THREAD INSERTION DEVICES

(71) Applicant: Allergan Industrie SAS, Pringy (FR)

(72) Inventors: Antoine Duc, Saint Jean le Vieux (FR); Bastien Mandaroux, Metz-Tessy (FR)

(73) Assignee: Allergan Industrie SAS, Pringy (FR)

( * ) Notice: Subject to any disclaimer, the term of this patent is extended or adjusted under 35 U.S.C. 154(b) by 203 days.

(21) Appl. No.: 15/414,248

(22) Filed: Jan. 24, 2017

(65) Prior Publication Data
US 2018/0206965 A1    Jul. 26, 2018

(51) Int. Cl.
*A61B 17/06* (2006.01)
*A61F 2/00* (2006.01)
(Continued)

(52) U.S. Cl.
CPC .. *A61B 17/06004* (2013.01); *A61B 17/06109* (2013.01); *A61F 2/0059* (2013.01); *A61B 17/06166* (2013.01); *A61B 17/3468* (2013.01); *A61B 2017/00792* (2013.01); *A61B 2017/00898* (2013.01); *A61B 2017/00942* (2013.01); *A61B 2017/06009* (2013.01); *A61B 2017/06042* (2013.01); *A61F 2210/0061* (2013.01)

(58) Field of Classification Search
CPC .... A61F 2/0059; A61F 2/105; A61B 17/3468; A61B 17/0482; A61B 17/06; A61B 17/06004; A61B 2017/06009; A61B 2017/06014; A61B 2017/06019; A61B 2017/06023; A61B 2017/06028; A61B 2017/06042; A61B 2017/06047; A61B 2017/06052
See application file for complete search history.

(56) References Cited

U.S. PATENT DOCUMENTS 1,250,114 A    12/1917    Bigelow et al.
1,558,037 A    10/1925    Morton
(Continued)

FOREIGN PATENT DOCUMENTS

EP    0648474 A1    4/1995
EP    0809968 A1    12/1997
(Continued)

OTHER PUBLICATIONS

Bleyer, Mark, SIS Facial Implant 510(k) Summary, Cook Biotech, Inc., May 19, 2005.

*Primary Examiner* — William H Matthews
(74) *Attorney, Agent, or Firm* — Nathan S. Smith; Danny Mansour; Morgan, Lewis & Bockius LLP

(57) ABSTRACT

Devices and methods for inserting an implant into skin or other tissue of a patient can include a hyaluronic thread that is coupled at along distal portion with an insertion device. The insertion device can include a cover member and a piston that can collectively facilitate engagement with or disengagement of the distal portion of the thread with the device. For example, the piston can be positioned within an inner cavity of the cover member, and the distal portion of the thread can be engaged by and/or between the piston and the cover member. The thread can be released by movement of the piston relative to the cover member. Thus, some insertion devices can grasp or engage the distal portion of the thread and "push" the distal portion thread into and through into skin or other tissue of a patient.

11 Claims, 11 Drawing Sheets

(51) Int. Cl.
*A61B 17/00* (2006.01)
*A61B 17/34* (2006.01)

(56) References Cited

U.S. PATENT DOCUMENTS

| | | | |
|---|---|---|---|
| 1,591,021 A | 7/1926 | Davis | |
| 2,092,427 A | 9/1937 | Frederick | |
| 2,302,986 A | 11/1942 | Vollrath | |
| 2,571,653 A | 10/1951 | Victor | |
| 3,204,635 A | 9/1965 | Voss | |
| 3,674,026 A | 7/1972 | Werner | |
| 3,910,282 A | 10/1975 | Messer et al. | |
| 4,402,308 A | 9/1983 | Scott | |
| 4,451,253 A | 5/1984 | Harman | |
| 4,820,267 A | 4/1989 | Harman | |
| 4,846,886 A | 7/1989 | Fey et al. | |
| 4,957,744 A | 9/1990 | della Valle et al. | |
| 4,994,028 A | 2/1991 | Leonard | |
| 5,116,358 A | 5/1992 | Granger et al. | |
| 5,211,644 A | 5/1993 | VanBeek et al. | |
| 5,215,535 A | 6/1993 | Gettig | |
| 5,254,105 A | 10/1993 | Haaga | |
| 5,258,013 A | 11/1993 | Granger et al. | |
| 5,304,119 A | 4/1994 | Balaban | |
| 5,350,385 A | 9/1994 | Christy | |
| 5,366,447 A | 11/1994 | Gurley | |
| 5,478,327 A | 12/1995 | McGregor et al. | |
| 5,599,293 A | 2/1997 | Orenga | |
| 5,735,827 A | 4/1998 | Adwers | |
| 5,752,970 A | 5/1998 | Yoon | |
| 5,824,335 A | 10/1998 | Dorigatti et al. | |
| 5,997,513 A | 12/1999 | Smith | |
| 6,102,920 A * | 8/2000 | Sullivan | A61B 17/062 |
| | | | 606/147 |
| 6,159,233 A | 12/2000 | Matsuzawa | |
| 6,162,203 A | 12/2000 | Haaga | |
| 6,214,030 B1 | 4/2001 | Matsutani et al. | |
| 6,450,937 B1 | 9/2002 | Mercereau | |
| 6,547,762 B1 | 4/2003 | Botich | |
| 6,936,297 B2 | 8/2005 | Roby et al. | |
| 7,041,088 B2 | 5/2006 | Nawrocki et al. | |
| 7,504,386 B2 | 3/2009 | Pressato et al. | |
| 7,559,952 B2 | 7/2009 | Pinchuk | |
| 7,666,339 B2 | 2/2010 | Chaouk et al. | |
| 7,722,582 B2 | 5/2010 | Lina et al. | |
| 7,998,170 B2 | 8/2011 | Cunningham | |
| 8,177,792 B2 | 5/2012 | Lubock | |
| 8,652,216 B2 | 2/2014 | Chen | |
| 9,801,688 B2 | 10/2017 | Jones | |
| 2001/0008937 A1 | 7/2001 | Callegaro et al. | |
| 2001/0050084 A1 | 12/2001 | Knudson | |
| 2002/0026039 A1 | 2/2002 | Bellini et al. | |
| 2003/0023250 A1 | 1/2003 | Watschke | |
| 2003/0097079 A1 | 5/2003 | Garcia | |
| 2003/0109769 A1 | 6/2003 | Lowery | |
| 2004/0192643 A1 | 9/2004 | Pressato et al. | |
| 2005/0033362 A1 | 2/2005 | Grafton | |
| 2005/0075606 A1 | 4/2005 | Botich | |
| 2005/0182446 A1 | 8/2005 | DeSantis | |
| 2006/0041320 A1 | 2/2006 | Matsuda | |
| 2006/0136070 A1 | 6/2006 | Pinchuk | |
| 2008/0119876 A1 | 5/2008 | Price et al. | |
| 2008/0125766 A1 | 5/2008 | Lubock | |
| 2008/0139928 A1 | 6/2008 | Lubock | |
| 2008/0167674 A1 | 7/2008 | Bodduluri et al. | |
| 2009/0131908 A1 | 5/2009 | McKay | |
| 2009/0209804 A1 | 8/2009 | Seiler | |
| 2009/0318875 A1 | 12/2009 | Friedman | |
| 2010/0256596 A1 | 10/2010 | Chomas | |
| 2011/0093088 A1 | 4/2011 | Chen | |
| 2011/0152926 A1 | 6/2011 | Vetrecin | |
| 2011/0263724 A1 | 10/2011 | Gurtner et al. | |
| 2011/0282447 A1 | 11/2011 | Niu | |
| 2012/0108895 A1 * | 5/2012 | Neuman | A61B 17/06109 |
| | | | 600/37 |
| 2012/0215230 A1 | 8/2012 | Lubock et al. | |
| 2012/0245629 A1 | 9/2012 | Gross et al. | |
| 2013/0122068 A1 | 5/2013 | Fermanian et al. | |
| 2013/0211374 A1 | 8/2013 | Hetherington | |
| 2013/0226235 A1 | 8/2013 | Fermanian et al. | |
| 2013/0274222 A1 | 10/2013 | Horne et al. | |
| 2013/0310750 A1 * | 11/2013 | Hopman | A61M 1/008 |
| | | | 604/159 |
| 2014/0221940 A1 | 8/2014 | Clauson et al. | |
| 2014/0228971 A1 | 8/2014 | Kim | |
| 2015/0209265 A1 | 7/2015 | Horne | |
| 2015/0209523 A1 | 7/2015 | Horne et al. | |
| 2015/0327972 A1 | 11/2015 | Horne et al. | |
| 2016/0007990 A1 | 1/2016 | Solish et al. | |
| 2016/0074307 A1 | 3/2016 | Gurtner et al. | |
| 2016/0213813 A1 | 7/2016 | Gurtner et al. | |
| 2017/0049972 A1 | 2/2017 | Persons | |
| 2017/0156754 A1 | 6/2017 | Valbuena | |
| 2017/0290987 A1 | 10/2017 | Mandaroux et al. | |
| 2018/0206963 A1 | 7/2018 | Duc et al. | |
| 2018/0206964 A1 | 7/2018 | Duc et al. | |
| 2018/0206966 A1 | 7/2018 | Duc et al. | |
| 2018/0206967 A1 | 7/2018 | Duc et al. | |

FOREIGN PATENT DOCUMENTS

| | | |
|---|---|---|
| EP | 2422832 A2 | 2/2012 |
| EP | 2103262 B1 | 2/2013 |
| EP | 2184016 | 4/2013 |
| EP | 2671516 | 12/2013 |
| GB | 2336783 A | 5/2003 |
| KR | 20120007473 | 1/2012 |
| KR | 101246570 | 3/2013 |
| KR | 20130036921 | 4/2013 |
| KR | 20130130436 | 12/2013 |
| KR | 20130132196 | 12/2013 |
| KR | 20140029007 | 3/2014 |
| WO | 199001349 A1 | 2/1990 |
| WO | 1992013579 A1 | 8/1992 |
| WO | 200100190 A2 | 1/2001 |
| WO | 2004022603 A1 | 3/2004 |
| WO | 2006065837 A2 | 6/2006 |
| WO | 2010028025 A1 | 3/2010 |
| WO | 2011109129 A1 | 9/2011 |
| WO | 2011109130 A1 | 9/2011 |
| WO | 2012054301 A1 | 4/2012 |
| WO | 2012054311 A1 | 4/2012 |
| WO | 2013055832 A1 | 4/2013 |
| WO | 2013082112 A1 | 6/2013 |
| WO | 2012174464 A3 | 5/2014 |
| WO | 2015105269 A1 | 7/2015 |

* cited by examiner

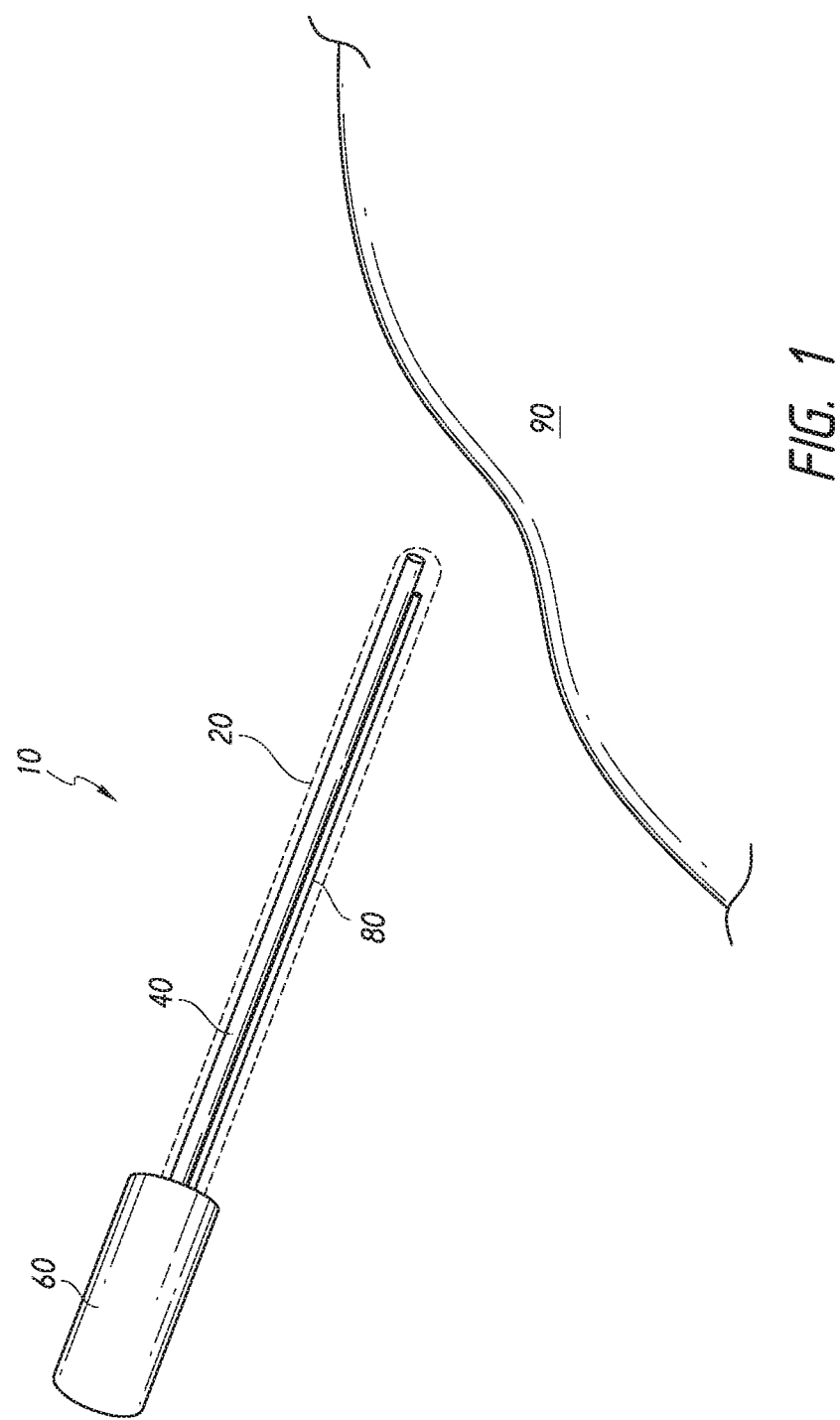

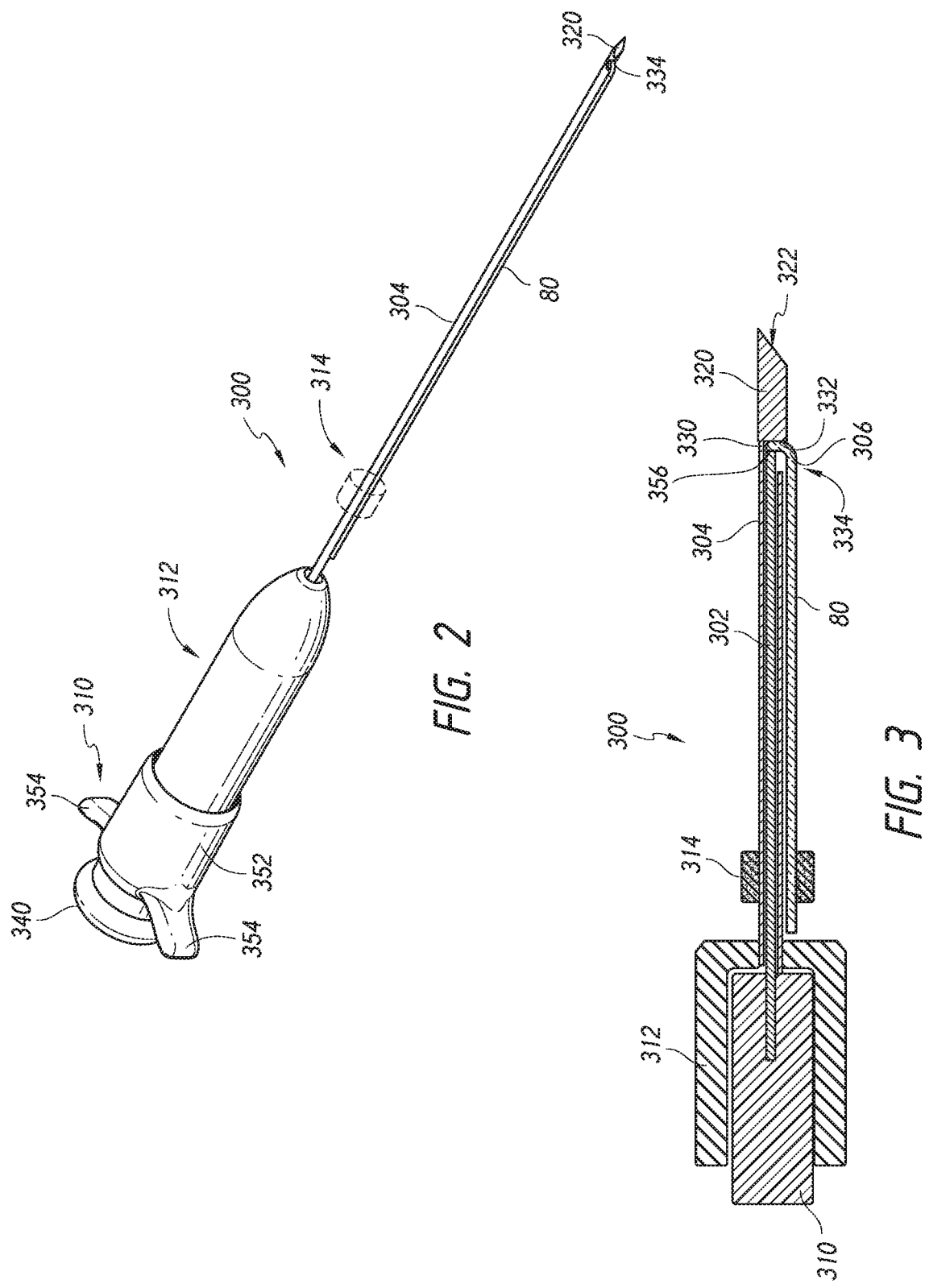

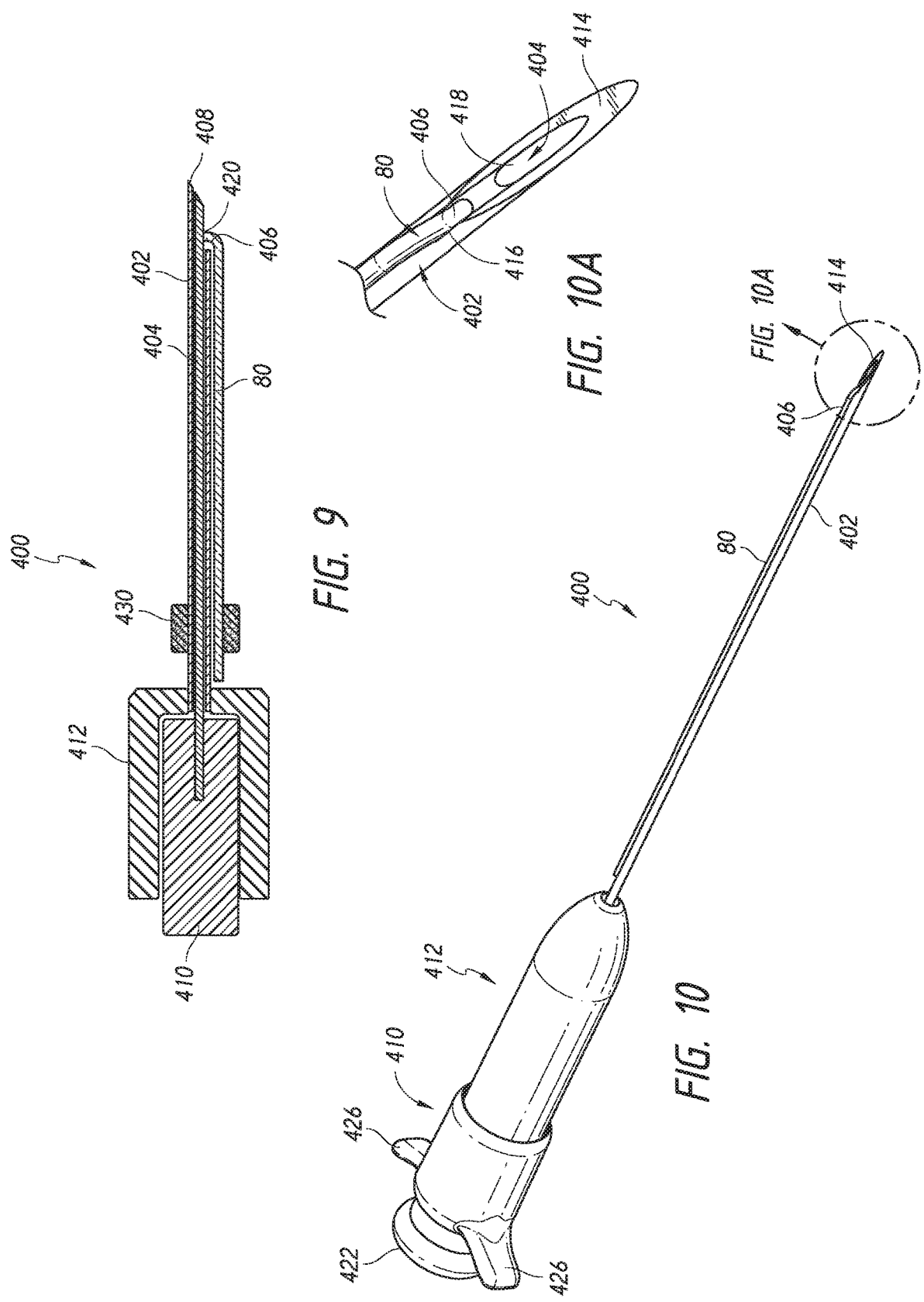

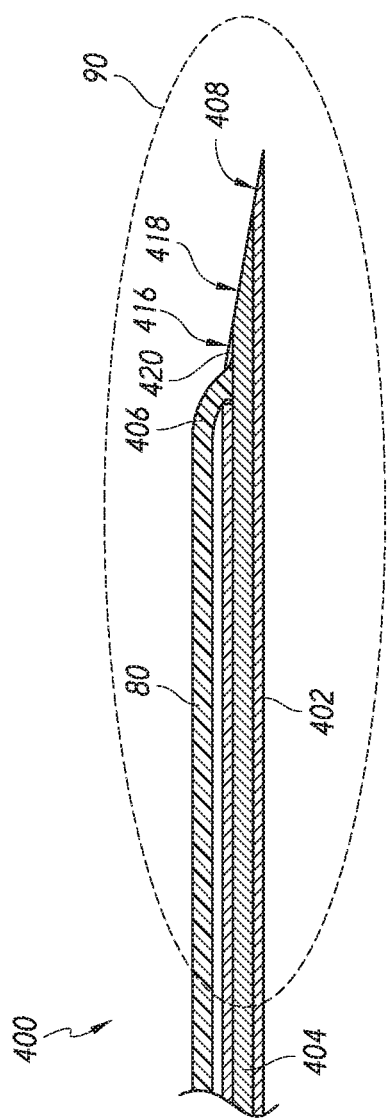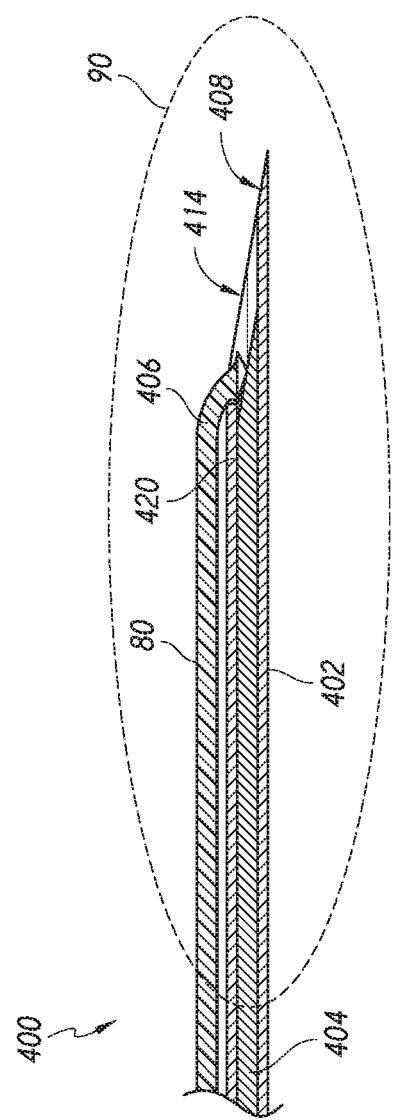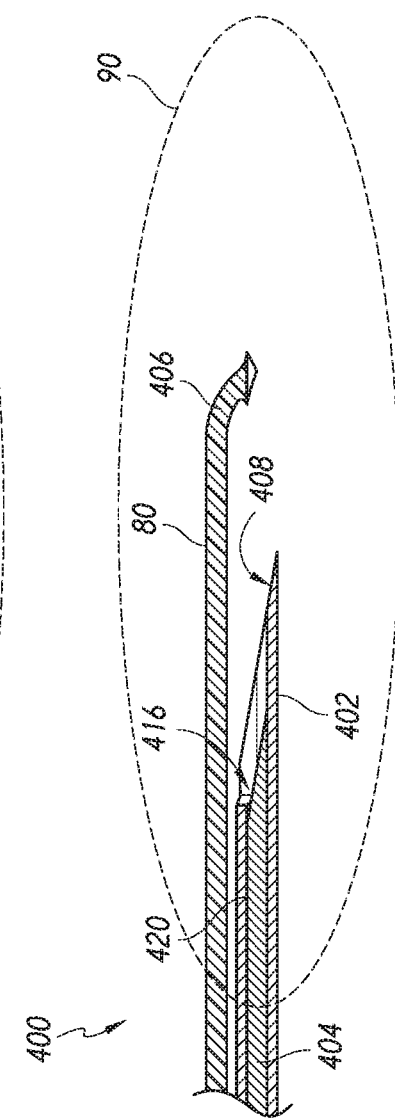

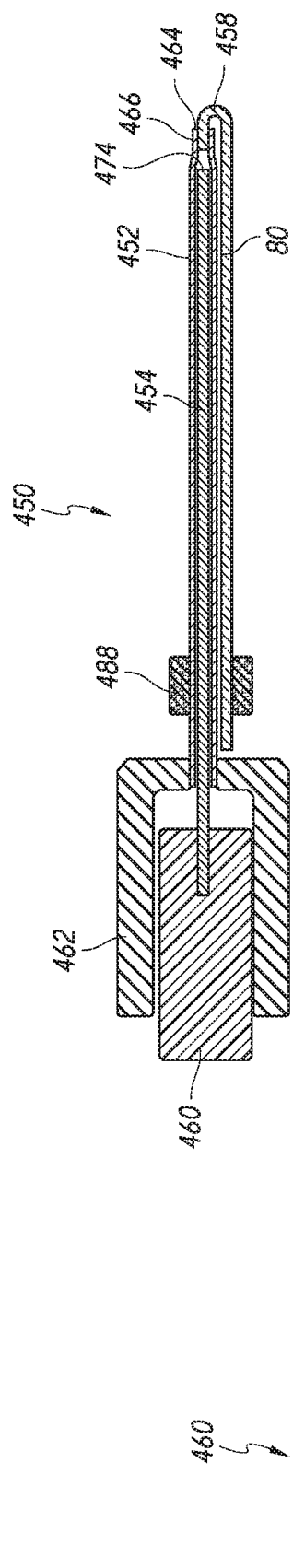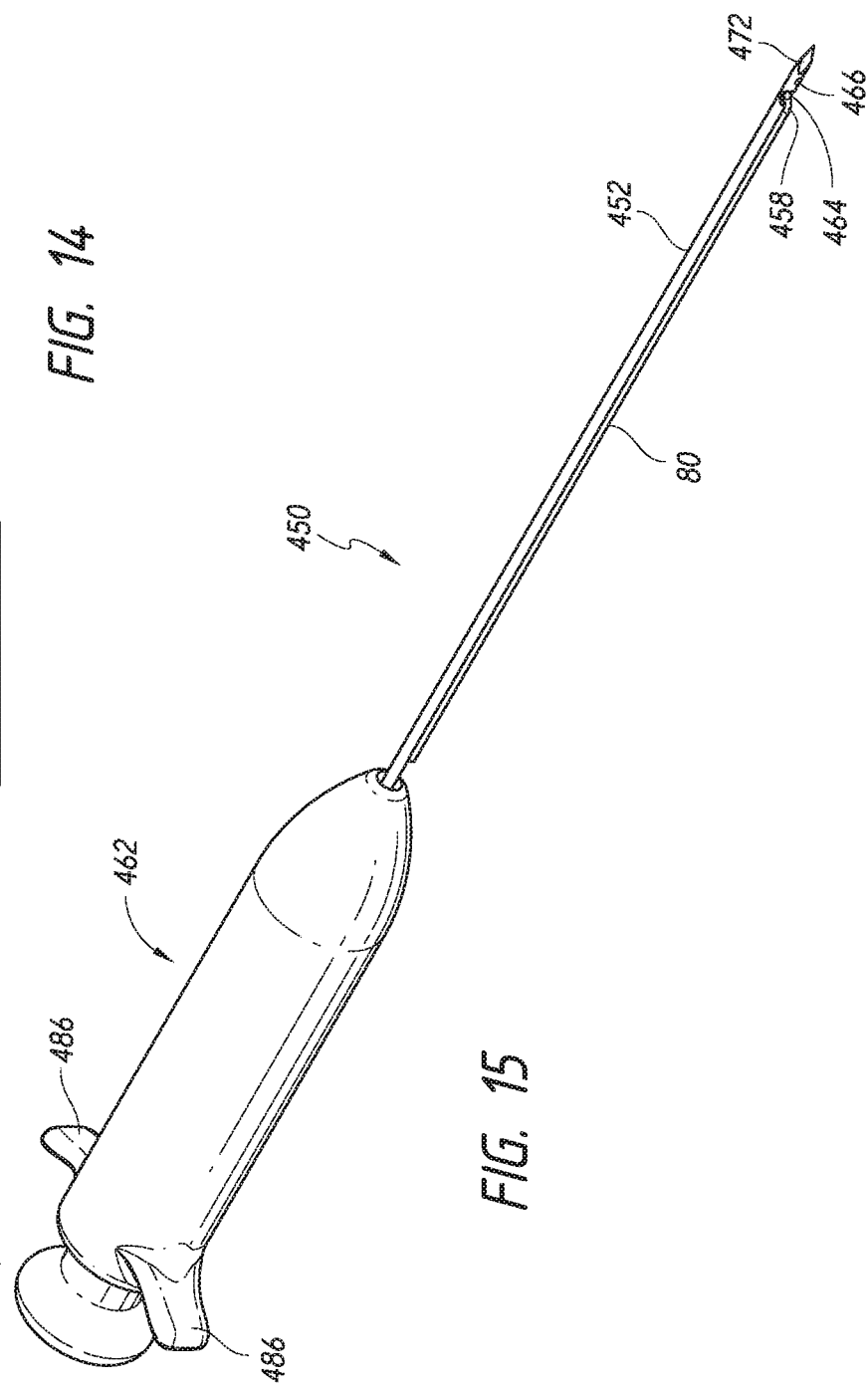

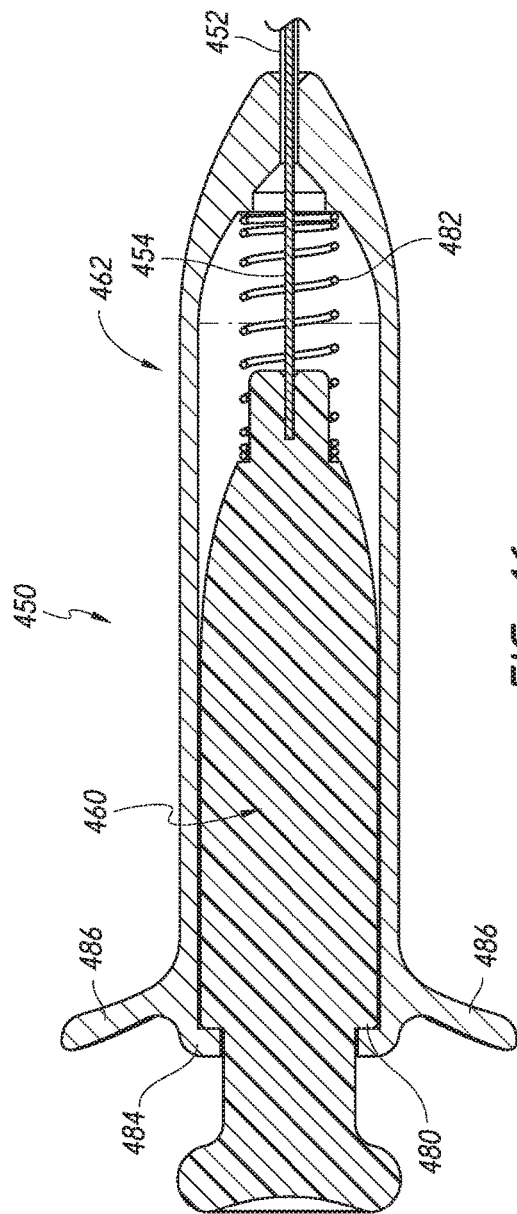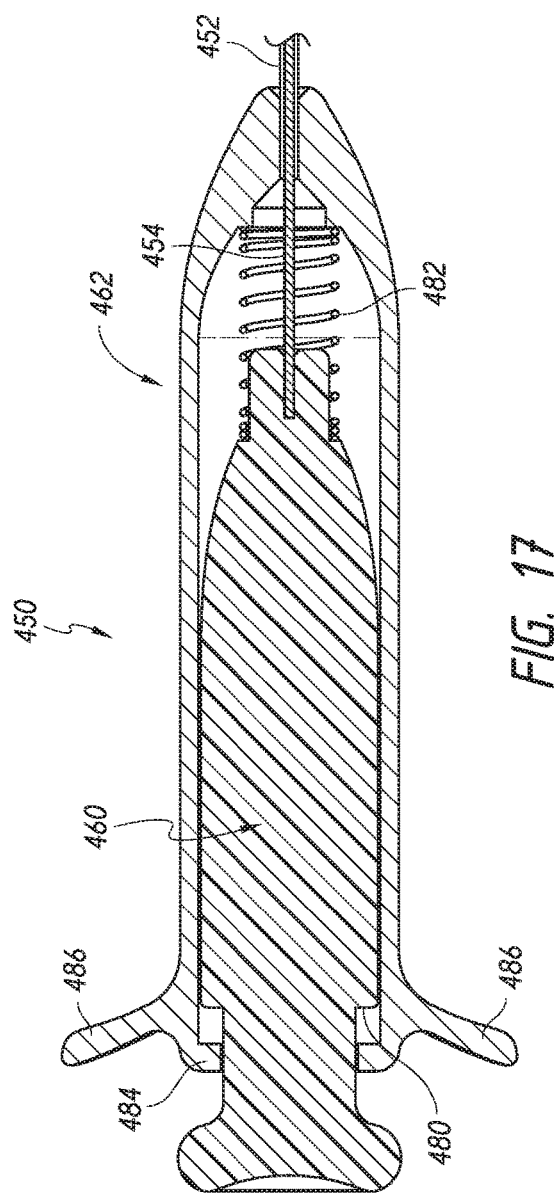
FIG. 16
FIG. 17

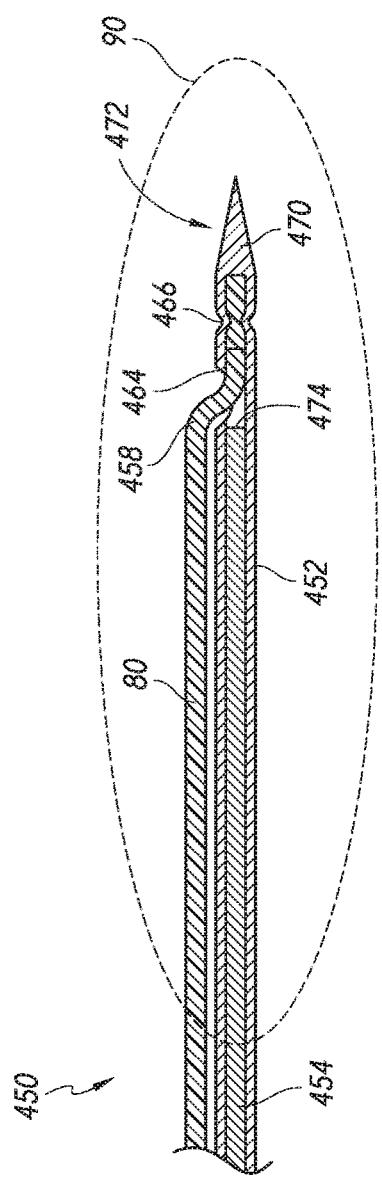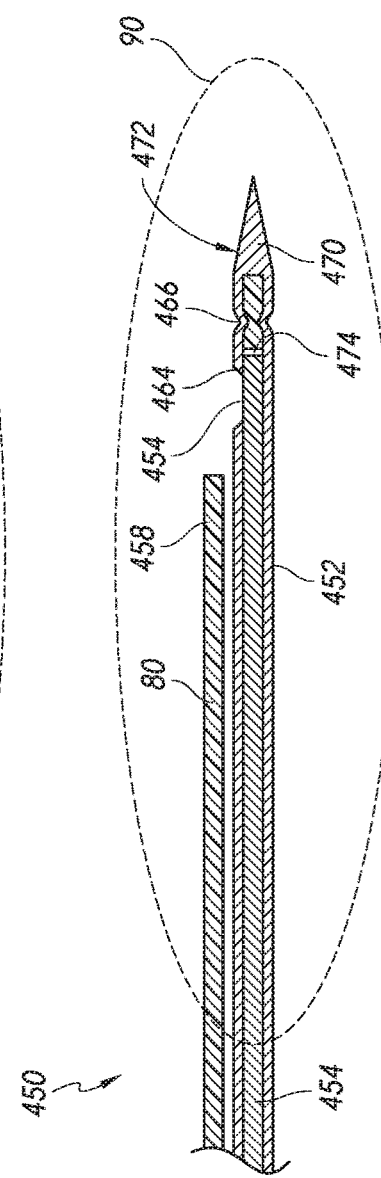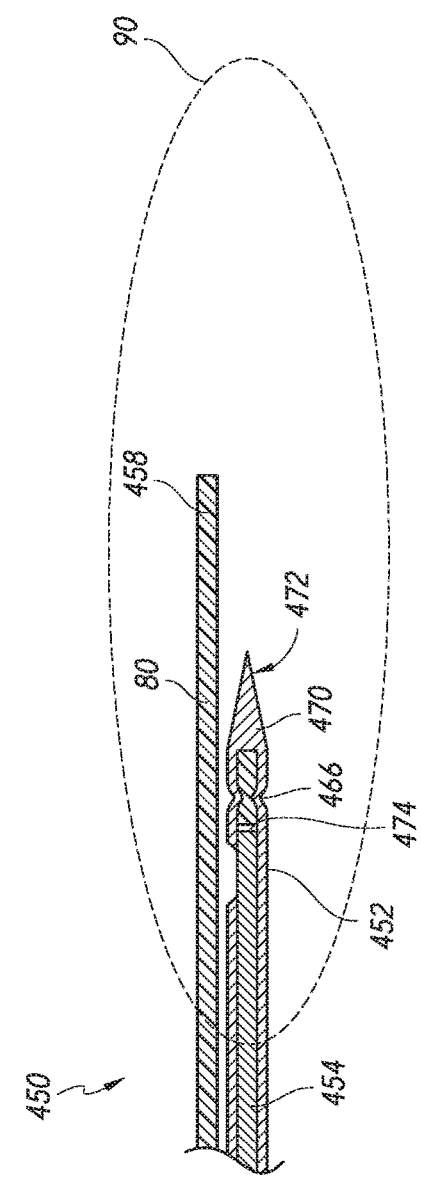

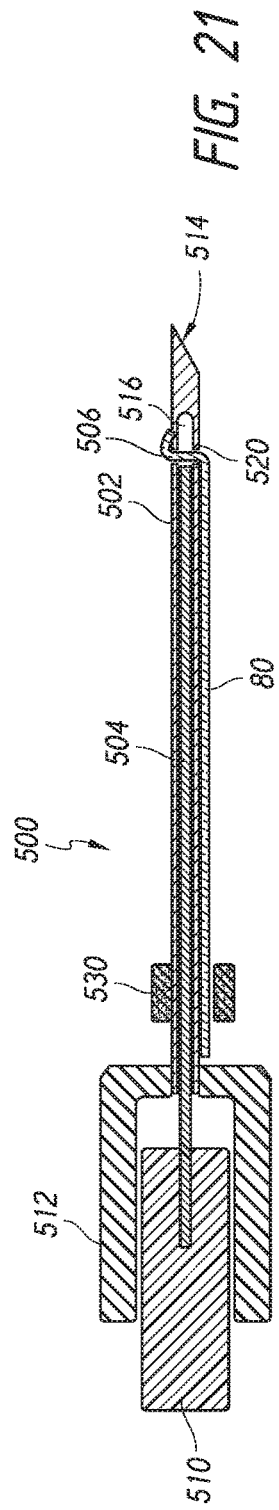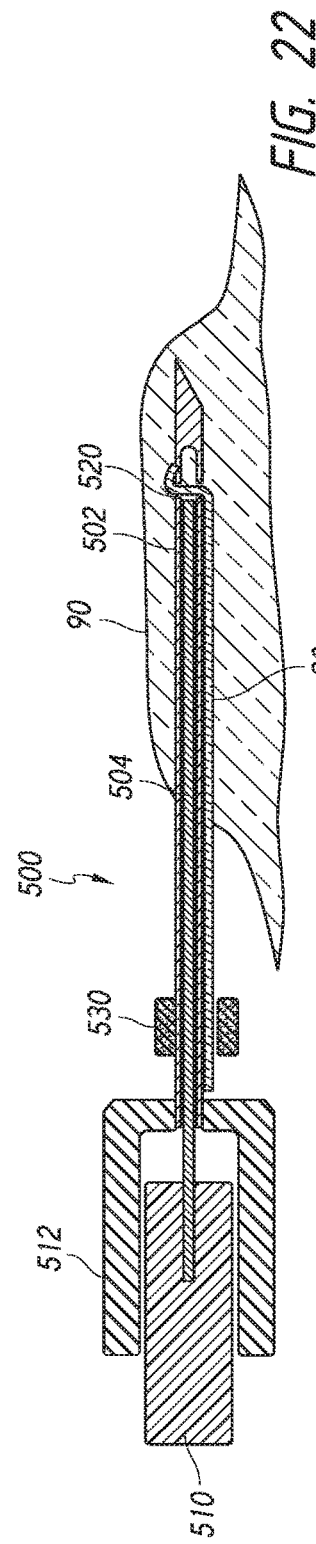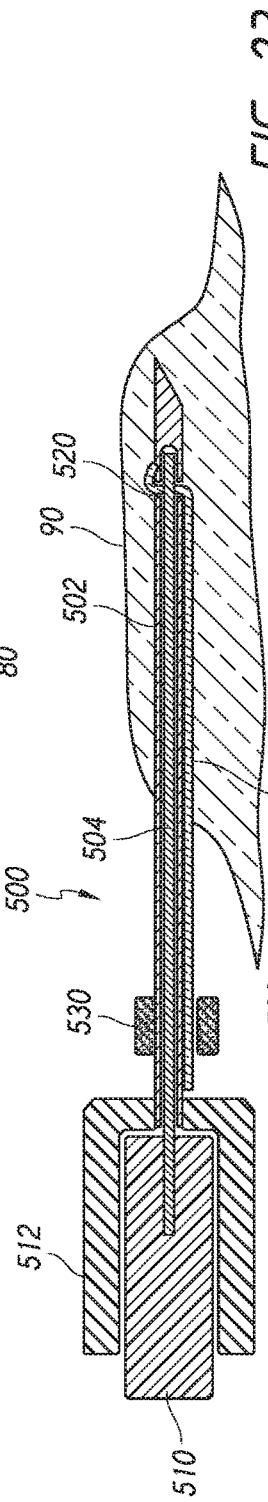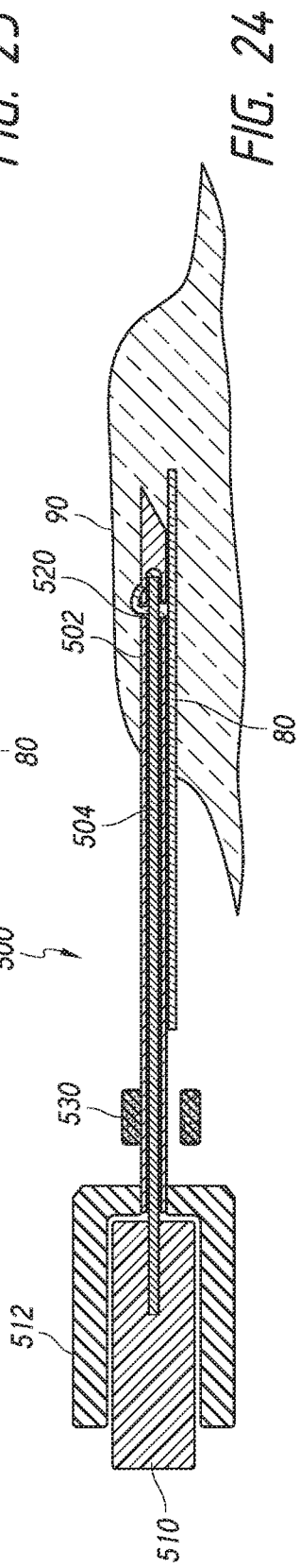

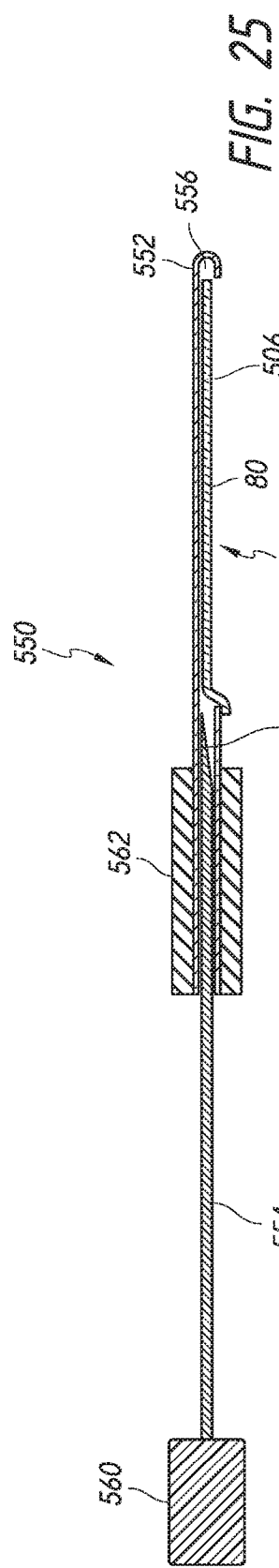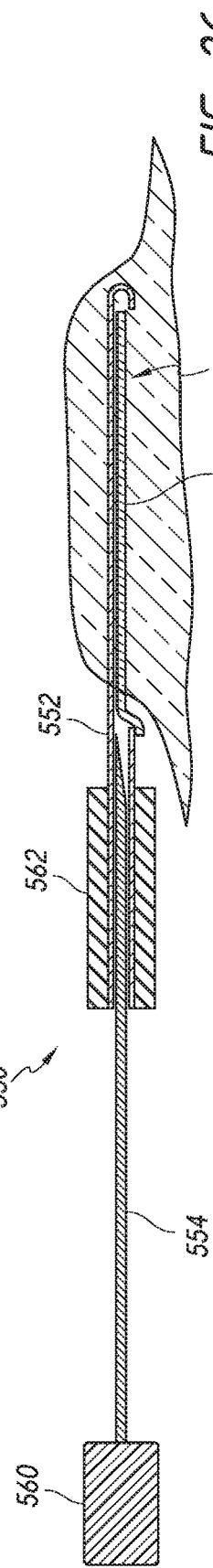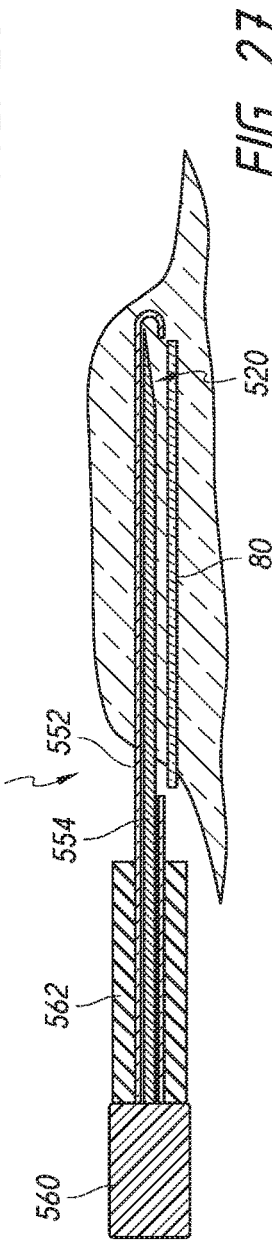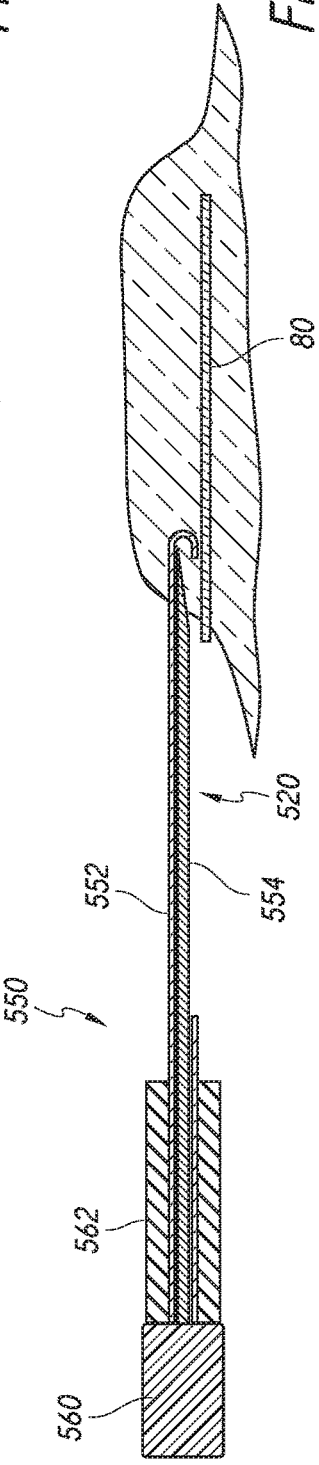

THREAD INSERTION DEVICES

BACKGROUND

Field of the Inventions

The present disclosure relates generally to systems and methods for insertion of an implant, and more particularly, to insertion devices that can grasp or engage a distal portion of a thread and "push" the distal portion thread into and through into skin or other tissue of a patient.

Background

In recent years, millions of men and women have elected to receive dermal filler injections to rejuvenate aging skin and look younger without surgery or significant downtime. A dermal filler injection is a procedure through which a gel-like, volumizing substance is injected subcutaneously to restore lost volume, add volume to facial features and contours, or smooth fine lines and creases.

Some dermal filler injections are performed using a thread or other implant. Once inserted, the threads used for dermal filler injections can hydrate and expand or swell within the skin of a patient, thereby lessening the appearance of wrinkles, folds, and/or sagging portions of skin.

To insert a thread into the patient, conventional suture procedures can be implemented. For example, using a conventional procedure, a physician couples a thread to a needle and inserts the needle through the skin until achieving a desired placement, which may be adjacent to or under a wrinkle. With the thread placed along or underneath the wrinkle, the needle can be removed and as the thread hydrates, the wrinkle can be "filled" and become less prominent, thus smoothing the skin and achieving a desired aesthetic for the patient.

SUMMARY

The present application discloses various improvements for thread insertion devices and related procedures that can be used to treat humans and/or animals. The devices and procedures can be used, for example, in the context of dermal fillers, surgery (e.g., placing sutures), drug delivery, negative pressure wound therapy, and wound dressing.

In plastic surgery, hyaluronic acid is a common substance used for wrinkle filling. Although hyaluronic acid is typically used as a gel that is injected as a wrinkle filler, some embodiments disclosed herein can utilize hyaluronic acid in a solid form as an implant, e.g., as a hyaluronic acid thread ("HA thread" or "thread").

However, in accordance with some embodiments disclosed herein in the realization that because HA threads are hydrophilic, the mechanical integrity of the thread can rapidly degrade during an implantation procedure. Thread failure can result in improper placement or other complications during the procedure. Thus, a thread that is exposed during insertion of the thread into a patient can become hydrated, causing the thread to swell or expand prematurely and/or lose its tensile strength. If the thread swells within a needle or insertion device, the thread will become lodged within the needle and unable to move relative to the insertion device. The thread can therefore block the needle lumen, prevent separation of the thread from the insertion device, or otherwise complicate the thread placement procedure. In some instances, the swelling of a thread may cause it to engage with skin tissue before the thread has reached a desired position subcutaneously. Thus, the thread becomes immovable during insertion of the thread into the patient. Further, during insertion, friction between the thread and the tissue may increase beyond a tensile strength of the thread and cause the thread to break and separate from the insertion device.

Further, some embodiments of the present devices and methods also contrast with various conventional thread placement devices that include a needle tip that engages a thread at its midsection and allows the thread to fold backwardly or proximally along a length of the needle. In accordance with some embodiments disclosed herein in the realization that because the thread is divided into two strands that extend along the length of the needle, the injection also results in a double-stranded thread placement in which the two strands will swell in situ. Although this may be acceptable in some applications, these conventional devices and procedures are limited because they have a "minimum expansion size" of twice that of a single thread. Accordingly, some of the embodiments disclosed herein enable a single strand of thread to be placed along a desired position instead of the conventional double-stranded thread placement. Advantageously then, some embodiments allow for a lower "minimum expansion size" that can allow a physician to treat wrinkles that are not otherwise good candidates for treatment using only the conventional devices or methods.

Further, because some embodiments disclosed herein "push" a distal portion or distal end of the thread through the skin, the physician need only to make a single piercing instead of entry and exit piercings required by conventional devices and methods that use a needle whose proximal end attaches to a distal portion of the thread and pushes the distal portion of the thread through the entry and exit piercings.

Therefore, some embodiments of the thread insertion devices and procedures disclosed herein can advantageously minimize the number of piercings through the skin, reduce the risk of thread contamination during the insertion procedure, and/or minimize pain and bruising to the patient. Further, some embodiments of the thread insertion devices and procedures disclosed herein can advantageously avoid breakage of the thread during insertion, facilitate safer and easier insertion of the thread, and/or permit greater control over the thread length and insertion depth.

Although particular embodiments of the present disclosure may be disclosed in the context of an implant comprising a thread, it is contemplated that embodiments can be used with various implants. For example, embodiments can be used with an implant comprising a thread, a series of hinged members, or a tube. Further, embodiments can comprise an implant comprising a rigid material, a flexible material, HA threads material, and a material comprising a state of matter including solid, liquid, or any state there between. The implant can comprise a medication and/or medical fluid that are configured to be released by the implant.

In some embodiments, the thread insertion device can comprise a cover member configured to protect an implant, or portions of a device that will be inserted into a patient. The cover member can prevent contamination or damage to a thread. The cover member can also maintain a shape or alignment of a thread relative to a thread insertion device.

The cover member can comprise a cavity or passage configured for a thread to be positioned therein. For example, the cover member can retain at least a portion or an entirety of the thread within a cavity or passage. Contamination or damage to the thread can be prevented when the thread is positioned within a cavity or passage of the cover member. The cover member can prevent contamination of the thread from exposure to an ambient environment, or from a person touching the thread. Further, damage to the thread can be avoided by preventing inadvertent touching or engagement of the thread. Damage to the thread can also be avoided by preventing exposure of the thread to moisture from the patient's skin or tissue, e.g., dermis, epidermis, and subcutaneous tissue, during insertion of the thread.

In some embodiments, the cover member can permit a thread to be positioned along an outer surface of the cover member. The cover member can permit a thread to be positioned along an inner surface of the cover member. The cover member can also provide support to maintain alignment of the thread during insertion.

In some embodiments, the thread can be retained and/or engaged with the cover member and/or a portion of the thread insertion device. Further, the cover member and/or a portion of the thread insertion device can be used to move a thread relative to the insertion device or separate a thread from the insertion device.

For example, the insertion device can comprise one or more portions that extend along an outer surface and/or within the cover member. The thread insertion device can comprise a moveable member within the cover member. A piston can be positioned within a cavity of the cover member. The piston can cause movement of the thread supported on or coupled with the insertion device. Movement of a portion of the insertion device, e.g., the cover member and/or the piston, can release or separate a thread from the insertion device.

In some embodiments, the thread insertion device can comprise a cover member that can be engaged against a thread to retain the thread with the insertion device. A portion of the cover member can be crimped, or compressed, or adhered to engage a portion of a thread. The thread can be adhered to the cover member. To release a thread from the insertion device, a portion of the cover member engaged against a thread can be moved or expanded, or the thread can be separated from the portion of the cover member.

The cover member can comprise a flexible or rigid body. The body can comprise a cross-sectional profile that defines a cavity. A shape of a cross-sectional profile of the cover member can comprise an open perimeter, a closed perimeter, a circle, a square, a rectangle, an L-shape, and/or a U-shape. The cover member can comprise an inner surface cross-sectional profile having portions that are tubular along a length of the cover member.

A portion of the cover member can comprise an opening, e.g., a channel or an aperture, between an inner cavity and an outer surface of the cover member. The cover member can permit a thread to be moved through the opening. A thread can be coupled to the insertion device by a portion of the thread that extends through the opening.

The cover member can comprise a proximal portion and a distal portion. The proximal portion can comprise an opening into a cavity of the cover member. The proximal portion can be coupled to other portions of the thread insertion device. The proximal portion can be releasably coupled to a portion of the insertion device.

A cavity of the cover member can extend toward the distal portion of the cover member. The cavity can extend toward a closed distal portion of the cover member. The distal portion of the cover member can comprise a tip portion. The tip portion can comprise an outer surface that tapers toward a point. A tapered or pointed tip can permit the cover member to pierce the patient's skin or tissue to allow insertion of the cover member and thread. The tip can comprise a point, a bevel, or a multiple-sided cutting point, e.g., a pin, a needle, or a trocar. The tip portion can comprises an outer surface that is rounded or blunt. A round or blunt tip can permit insertion of the cover member through an opening of a patient without piercing or causing damage to the patient.

The thread insertion device can comprise a piston configured to engage a thread against a portion of the insertion device. In some embodiments, the piston can engage against a portion of the insertion device. The piston can be configured to retain and/or release a thread from the insertion device. The piston can be configured to engage a thread to maintain a shape and alignment of the thread relative to the insertion device. The piston can be configured to position or direct the location where a thread is to be implanted. A thread can be engaged between a piston and a cover member. A flexible cover member can extend around the piston to retain a thread between the flexible cover member and the piston.

The piston can comprise a proximal portion and a distal portion. The proximal portion can comprise a base or other feature configured to be engaged by a physician to move the piston relative to the thread insertion device. The distal portion of the piston can extend through a cavity or passage of a cover member, or along an outer surface of a cover member.

A portion of a thread can be coupled to the second portion of the piston. The thread can be separated from the second portion of the piston when the piston is moved relative to the insertion device. Optionally, a portion of the thread can extend through an opening or aperture of a cover member, wherein the portion of the thread can be coupled to the piston. To separate the thread from the piston, the piston can be moved relative to the cover member.

A portion of a thread can be engaged between the piston and a portion of the insertion device. The thread can be engaged between the distal portion of the piston and a cover member. Optionally, a portion of the thread can extend through an opening or aperture of the cover member, and be engaged between the piston and an inner surface of the cover member. To separate the thread from the insertion device, the piston can be moved relative to the cover member. In some embodiments, movement of the piston can cause the distal portion the piston to move away from the cover member, thereby releasing the thread.

To release or separate the thread from the insertion device, the piston can move a portion of the insertion device. A portion of the thread can be compressed or pinched by a cover member. To release the thread, the piston can be moved to engage and urge the cover member away from the portion of the thread engaged by the cover member.

The thread insertion device can comprise a resilient biasing member, e.g., a spring, between portions of the insertion device. The biasing member can be positioned between a piston and a portion of the insertion device. The biasing member can urge a piston in a first direction so that movement of the piston in a second direction, opposite the first direction, causes a thread to be separated from the insertion device. The piston can be urged in a first direction relative to a cover member. The first direction can be toward or away from the cover member. The biasing member can be configured to urge the piston toward a distal portion of a cover member, or away from a distal portion of a cover member.

The insertion device can comprise a first base, a second base, and a biasing member. Each of the first and second bases can be configured to comprise a proximal portion and a distal portion, opposite the proximal portion. A piston can be coupled to the distal portion of the first base, and a cover member can be coupled to the distal portion of the second base. Optionally, a portion of the first base can be positioned within a cavity of the second base, such that a distal portion of the piston is adjacent to a distal portion of the cover member. To urge the distal portion of the piston toward the distal portion of the cover member, a biasing member can be positioned between the first portions of the first and second base. To urge the distal portion of the piston away from the distal portion of a cover member, a biasing member can be positioned between the second portions of the first and second base.

The thread insertion device can comprise a fastener, e.g., a band, loop, strap, or clip, to retain a portion of a thread adjacent to the insertion device. The fastener can engage a portion of a thread against the insertion device. The band can be used to retain a thread prior to use the insertion device, or can remain with the insertion device during delivery procedure, and removed to release the thread. The band can extend around an outer surface of the insertion device, with a portion of a thread positioned between the band and the insertion device. Optionally, the band extends around an outer surface of a cover member with a portion of the thread extending between the cover member and the band. The band can comprise a flexible material, an adhesive tape, and/or a hook and loop fastener.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures:

FIG. 1 is a front view of an insertion device, according to some embodiments.

FIG. 2 is a front perspective view of an insertion device, according to some embodiments.

FIG. 3 is a cross-sectional side view of an insertion device, according to some embodiments.

FIG. 9 is a cross-sectional side view of an insertion device, according to some embodiments.

FIG. 10 is a front perspective of an insertion device, according to some embodiments.

FIG. 10A is a detail view of a needle of an insertion device, according to some embodiments.

FIGS. 11-13 are cross-sectional side detail views of an insertion device, according to some embodiments.

FIG. 14 is a cross-sectional side view of an insertion device, according to some embodiments.

FIG. 15 is a front perspective view of an insertion device, according to some embodiments.

FIGS. 16-20 are cross-sectional side detail views of an insertion device, according to some embodiments.

FIGS. 21-24 are cross-sectional side views of an insertion device, according to some embodiments.

FIGS. 25-28 are cross-sectional side views of an insertion device, according to some embodiments.

DETAILED DESCRIPTION

Figure 4:
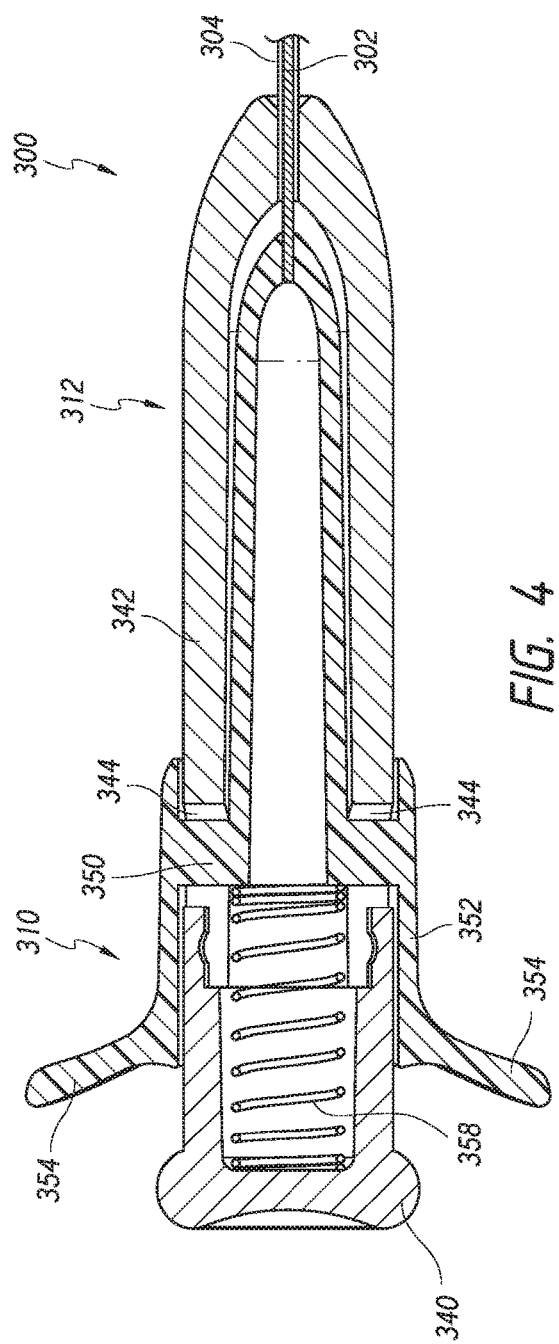
FIGS. 4-8 are cross-sectional side detail views of an insertion device, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of HA thread insertion devices, such embodiments can be used with various devices and implants. Furthermore, various applications of such embodiments and modifications thereto, which may occur to those who are skilled in the art, are also encompassed by the general concepts described herein.

The present application addresses several operational challenges encountered in prior HA thread insertion devices and related procedures. This application provides numerous improvements that enable the physician to control the device more easily, thereby allowing precise positioning of the implant while minimizing trauma to the patient.

For example, in accordance with some embodiments, the present application discloses various features and advantages of thread insertion devices and procedures that can be used to deliver an implant into skin or other tissue of a patient. The thread insertion device can avoid contamination a HA thread and protect the thread's mechanical properties during insertion. The thread insertion device can also permit a physician to precisely position the implant while minimizing trauma to the patient. The present disclosure, along with co-pending U.S. patent application Ser. Nos. 15/414,195, 15/414,278, 15/414,219, and 15/414,306, each filed on the same day as the present application, includes various features that can be interchangeably implemented into embodiments of thread insertion devices and methods of their use and the contents of these applications are incorporated herein in by reference in their entireties. For example, various aspects of the engagement mechanisms, actuation components, cover members, handles, and other features for delivering, protecting, engaging, advancing, or otherwise handling a needle and/or thread, can be combined or substituted with features of embodiments disclosed herein.

Further, some embodiments of the thread insertion devices and procedures disclosed herein can advantageously allow a single strand of HA thread to be positioned in situ as opposed to conventional double-stranded thread placement. Some embodiments disclosed herein relate to push-type thread insertion devices that can grasp or engage a distal portion of a thread and "push" the thread into and through a treatment site of a patient. In some embodiments, the thread can be exposed. Further, once in position, the thread can be separated from the insertion device using an activation or separation component. Such devices and procedures can advantageously allow a single strand of thread to be positioned in situ as opposed to conventional double-stranded thread placement. This additional level of precision can provide improved techniques and results for the patient.

Referring to the figures, a schematic illustration of a general embodiment of a thread insertion device 10 is shown in FIG. 1. The insertion device 10 can comprise a cover member 20, a support member 40, and a base 60. A HA thread 80 can be positioned between the cover member 20 and the support member 40 (each of the embodiments discussed herein refers to the HA thread 80, but the HA thread 80 can be substituted, modified, or replaced in any of the embodiments with a thread or suture having a different type, length, and/or size).

The insertion device 10 comprises a proximal portion and a distal portion. The proximal portion comprises the base 60, and the distal portion comprises the cover member 20 and the support member 40. The base 60 can comprise one or more portions. The base 60 can comprise a first portion and a second portion that is movable relative to the first base portion. The base 60 can comprise a movable member, e.g., a button or engagement member, to permit a portion of the insertion device to be separated from the base 60.

The support member 40 can be coupled to the base 60 and extend from the base 60 toward the distal portion of the insertion device 10. The support member 40 can comprise a shaft, a rod, and/or a plate having a longitudinal length. A cross-section, transverse to the longitudinal length of the support member 40, can be non-tubular and/or tubular, and can comprise a shape or profile such as a circle, a square, a rectangle, an L-shape, and/or a U-shape.

The cover member 20, illustrated in broken lines, can extend around the outer surface of the support member 40. The cover member 20 can be coupled to the base 60. The cover member 20 can comprise a rigid material, a flexible material, or any combination thereof. In some embodiments, the cover member 20 can comprise any of a rigid material, such as stainless steel (e.g., 304 or grade 316L), titanium, an alloy of nickel and titanium (e.g., nitinol), and a synthetic fluoropolymer of tetrafluoroethylene such as Polytetrafluoroethylene (PTFE). A thread 80 can be positioned between the support member 40 and the cover member 20. The thread 80 can extend along a longitudinal length of the support member 40. The cover member 20 can prevent contamination or damage to the thread 80.

In accordance with some embodiments, a physician can hold the insertion device 10 by the base 60, and the distal portion of the device directed through the skin 90 of a patient so that a portion of the device and thread are positioned under the skin 90. The physician can advance the support member 40 and the cover member 20 into the skin 90 of the patient by piercing the skin 90 using a sharp portion of the support member 40 and/or the cover member 20. In some methods, the skin 90 of the patient can be pierced or cut open before directing the insertion device 10 into the patient.

Once the skin 90 has been pierced and the support member 40 and the thread 80 are positioned subcutaneously, the cover member 20 can be removed from the device 10. For example, the cover member 20 can be removed from the distal portion of the insertion device 10 before or after engaging the insertion device 10 against the skin 90. In some embodiments, the insertion device 10 can be configured so that the cover member 20 is removed from the distal portion as the insertion device 10 is inserted into the skin 90. Further, in some embodiments, the insertion device 10 can also or alternatively be configured so that the cover member 20 is inserted into the skin 90 and then removed. For example, the insertion device 10 can be configured so that a portion of the device, e.g., the cover member 20, is inserted through a first portion of the skin 90 and removed through a second portion of the skin 90. Additionally, in some embodiments, the cover member 20 can be left in situ after implantation and be partially or fully dissolvable within the skin 90.

As discussed above, some embodiments and procedures can advantageously allow a single strand of thread to be positioned in situ as opposed to conventional double-stranded thread placement. Some embodiments of the insertion devices and procedures disclosed herein can also be configured to permit the thread to be exposed during insertion into the skin. FIGS. 2-28 illustrate several embodiments of thread insertion devices and related procedures that can allow a distal portion of a HA thread to attach or be coupled to a distal portion of the insertion device, thereby allowing the insertion device to push the distal portion or distal end of the thread during the injection procedure.

Referring now to FIGS. 2-8, some embodiments of the insertion device can be configured to pinch, compress, attach, or otherwise engage a distal portion or distal end of the thread to "push" the thread to a desired position in situ and then to disengage with the distal portion of the thread from the device after the thread reaches the desired position. FIG. 2 illustrates a perspective view of a thread insertion device 300 that can pinch or compress a distal portion of a HA thread 80 in order to secure the thread relative to the device 300 during the injection procedure. FIG. 3 illustrates a schematic cross-sectional view of the insertion device 300.

As illustrated, the insertion device 300 can comprise a compression piston 302 and a cover member 304 that can be actuated to pinch or compress a distal portion 306 of the thread 80. The insertion device 300 can also comprise a first base 310 and a second base 312 that can be used to actuate the piston 302 and the cover member 304. For example, portions of the insertion device 300 can be moveable, including the piston 302, the cover member 304, the first base 310, and/or the second base 312. For example, the piston 302 and the first base 310 can be moveable relative to the cover member 304 and second base 312, to pinch or compress a distal portion 306 of the thread 80 or to release the thread 80 from engagement with the device 300.

The thread 80 can be coupled to the insertion device 300 and positioned to extend along an outer surface of the cover member 304. A longitudinal axis of the thread 80 can extend along the cover member 304 so that a proximal portion of the thread 80 is engaged against the proximal portion of the cover member 304, and a distal portion 306 of the thread 80 is engaged to distal portion of the cover member 304. The proximal portion of the thread 80 can be engaged against the outer surface of the cover member 304. The proximal portion of the thread 80 can be engaged by a fastener 314. A distal portion 306 of the thread 80 can extend through the aperture 334 of the cover member to be engaged by the piston 302 and/or the cover member 304.

The fastener 314 can be coupled to the insertion device 300 to extend around an outer surface of the cover member 304. The fastener can extend around an outer surface of the cover member and the thread, to retain the thread adjacent to the cover member. The fastener 314 can extend around the cover member and/or thread, each e.g., a band, loop, or strap, as illustrated in FIG. 2. The fastener 314 can extend around a portion of the cover member and/or thread, e.g., a clip or clam, as illustrated in FIG. 3.

Referring to FIG. 2, the cover member 304 can comprise a proximal portion and a distal portion. The cover member 304 comprises a longitudinal axis that extends between the proximal and distal portions. A portion of a longitudinal length of the cover member 304 can comprise a tubular shape. A cross-sectional profile transverse to the longitudinal length of the cover member 304 can comprise a circle, oval, regular or irregular polygon, square, and/or rectangle shape. The shape or size of the cover member 304 can vary along a length or width of the cover member.

The distal portion of the cover member 304 can comprise a tip portion 320 having a tapered outer surface. The tip portion 320 comprises an outer surface that tapers from the proximal end, e.g., a bevel 322. The tapered or pointed tip can permit the cover member 304 to pierce the patient's skin or tissue to allow insertion of the cover member 304. The tip portion 320 can comprise an outer surface that is rounded or blunt. A round or blunt surface can prevent damage to the patient's tissue during insertion of the cover member.

The cover member 304 comprises an inner cavity 330 that extends from the proximal portion toward the distal portion of the cover member 304. The inner cavity 330 can extend from the proximal portion of the cover member 304 to the tip portion 320. The inner surface of the cavity 330 can comprise a cross-sectional profile, transverse to a longitudinal axis of the cover member 304, having a circle, oval, regular or irregular polygon, square, and/or rectangle shape. The inner surface of the cavity 330 can have a profile that corresponds to the outer surface of the piston 302. The shape or size can vary along the length or width of the cavity 330. The inner cavity 330 is configured to permit the piston 302 to extend within the cavity 330 and move along the longitudinal axis of the cover member 304.

Further, the cover member can comprise a first thread engagement surface 332 disposed along a portion of the cavity 330. The first thread engagement surface 332 can comprise an inner surface of the cover member 304. The first thread engagement surface 332 can comprise a distal-most inner surface of the cavity 330.

The cover member 304 can comprise an aperture 334 configured to permit a portion of a thread to extend into the cavity 330. The aperture 334 can extend through a longitudinal wall of the proximal or distal portion of the cover member 304. The aperture 334 can extend through the distal portion of the cover member 304 adjacent to the tip portion 320, as illustrated in FIG. 3. The aperture 334 can extend transverse to the longitudinal axis of the cover member 304. In some embodiments, the aperture 334 can extend through a distal portion of the cover member 304. The aperture 334 can be adjacent to the first thread engagement surface 332. The aperture 334 is configured to permit a distal portion 306 of a thread 80 to extend through the opening and into the cavity 330 in order to permit the distal portion 306 of the thread 80 to be pinched or compressed with the device 300, for example, using the piston 302.

Figure 5:
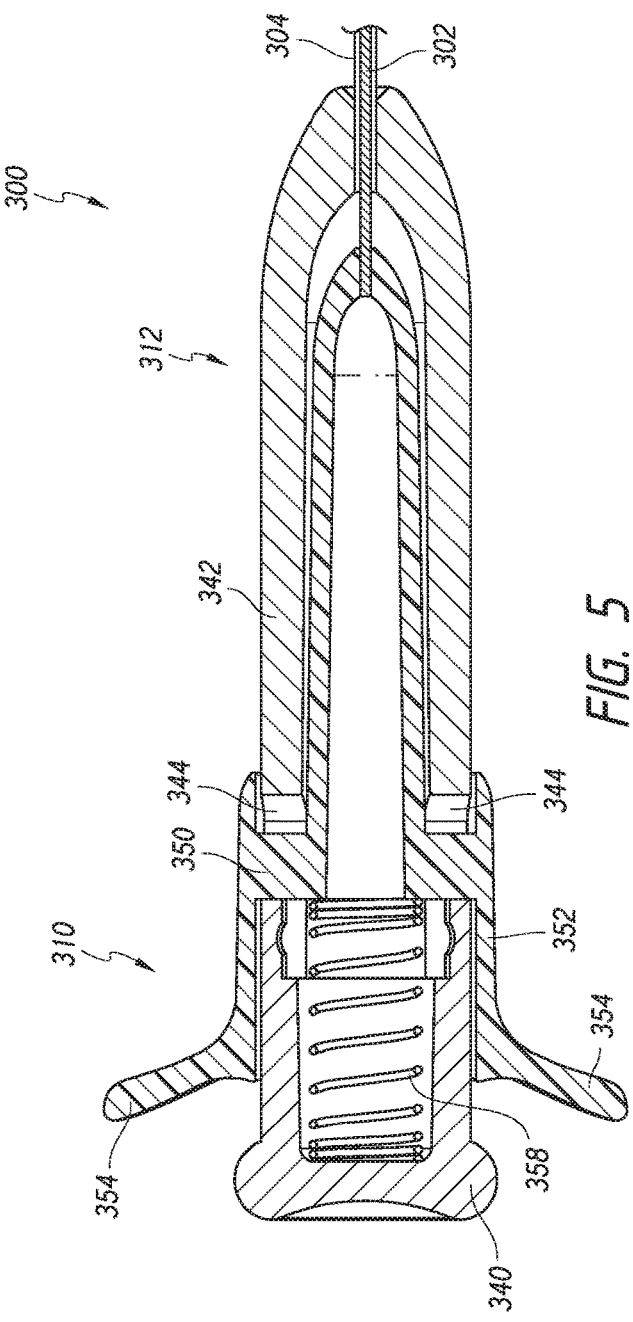

The proximal portion of the cover member 304 can be coupled to the second base 312. The second base 312 can comprise a proximal portion and a distal portion. The proximal and distal portions of the second base 312 can comprise a cavity that can extend within the proximal and distal portions. The proximal portion of second base 312 can comprise a proximal wall 340 having an outer surface and an inner surface facing the cavity, as illustrated in FIGS. 4 and 5. The inner surface of the proximal wall 340 can form a portion of the cavity, and the outer surface can be configured to be engaged by a portion of the physician's hand, e.g., a palm or finger. The proximal wall 340 can comprise a concave surface configured be engaged by a portion of the physician's hand.

The second base 312 can comprise a sidewall 342 that extends distally from the proximal wall 340 toward the distal portion of the second base 312. The sidewall 342 can comprise a channel 344 forming a passage that extends from the cavity to the outer surface of the second base 312. The channel 344 can extend along the proximal portion of the second base 312. The channel 344 can extend from a portion of the second base 312, between the proximal and distal portions, toward the proximal wall 340. In some embodiments, the channel 344 extends from the proximal wall 340 toward the distal portion of the second base 312. A portion of the first base 310 can extend through the channel 344. A portion of the first base 310 can be moved, relative to the second base 312, along the channel 344.

The distal portion of the second base 312 can be coupled to the proximal portion of the cover member 304, such that the cavity of the second base 312 is coupled to the cavity of the cover member 304. The cavity of the second base 312 and the cover member 304 form a passage that can extend from the second base 312 to the distal aperture 334 of the cover member 304. The cavity of the second base 312 is configured to permit a portion of the first base 310 and/or the piston 302 to be positioned therein. The cavity of the second base 312 is configured to permit the first base 310 and the piston 302 to move, relative to the second base 312 and the cover member 304.

The first base 310 comprises a proximal portion and a distal portion, opposite the proximal portion, and a longitudinal axis between the proximal and distal portions. The distal portion of the first base 310 comprises a cross-sectional profile transverse to the longitudinal axis that is configured to be positioned within the cavity of the second base 312.

The proximal portion of the first base 310 comprises an arm 350 that extend laterally, transverse to the longitudinal axis of the first base. The arm 350 can extend through the sidewall 342 of the second base. The first base 310 can comprise a pair of opposing arms 350 that extend through opposing channels 344. A portion of the arm 350 can be coupled to a sleeve 352.

The sleeve 352 can be a portion of the first base that extends along the sidewall 342 of the second base 312. The sleeve 352 can be a cylinder that extends around the outer perimeter of the second base 312. The sleeve 352 can have an inner surface having a cross-sectional profile that permits the sleeve to move along the outer surface of the second base 312. The inner surface of the sleeve 352 can be separated from the outer surface of the second base 312.

The sleeve 352 can positioned along the sidewall 342, between the proximal wall 340 and the distal portion of the second base 312. The sleeve 352 can be positioned along the proximal portion of the second base 312. The sleeve 352 can permit a physician to grasp the first base 310, and move the first base relative to the second base 312.

A flange 354 can extend from an outer surface of the sleeve 352. The flange 354 can be configured as a portion of the sleeve 352 comprising a ledge, lever, protrusion, knob, ring, groove, and/or ridge. The flange 354 can be configured to permit a physician to grasp the first base 310 with a hand or finger. The insertion device 300 can comprise a first and second flange 354. The first and second flanges 354 can extend laterally away from the sleeve 352 in opposing directions. In some methods, one or more finger of a physician, e.g., an index finger and a middle finger, can be engaged against one or more flange 354.

The piston 302 can comprise a proximal portion and a distal portion, opposite the proximal portion, and a longitudinal axis that extends between the proximal and distal portions. The distal portion of the piston 302 can comprise the second thread engagement surface 356 that can be used to pinch or compress a distal portion 306 of the thread 80. The second thread engagement surface 356 can comprise a distal end surface of the piston 302. The piston 302 is coupled to the first base 310 and can extend within the cavity of the cover member 304. The piston 302 can comprise a shaft, a rod, and/or a plate having a longitudinal length between a proximal portion and a distal portion. The distal portion of the piston 302 can extend within the cavity of the cover member 304 and can be moved along a longitudinal axis of the cover member 304.

A cross-sectional profile transverse to the longitudinal axis of the piston 302 can comprise a circle, oval, regular or irregular polygon, square, and/or rectangle shape. The shape or size can vary along the length or width of the piston 302. The outer surface of the piston 302 can have a profile that corresponds to the cavity of the cover member 304. In some embodiments, the outer surface of the piston 302 can comprise a smaller profile shape than the inner surface of the cover member 304.

A length of the piston 302, from the of the first base 310 to the second thread engagement surface 356, can be equal to or greater than a length of the passage from the second base 312 to the first thread engagement surface 332 of the cover member 304. The length of the piston 302 can permit the portion of the piston comprising the second thread engagement surface 356 to extend along the portion of the cover member comprising the aperture 334.

A resilient biasing member 358, e.g., a spring, can bias the first and second bases 310, 312 relative to each other. The biasing member 358 can comprise a proximal portion and a distal portion. The distal portion of the biasing member 358 can engage the first base 310, and the proximal portion of the biasing member 358 can engage the second base 312.

The biasing member 358 can be positioned between the first base 310 and the second base 312 to urge the first base 310 toward the distal portion of the second base 312. To urge the first base 310 toward the distal portion of the second base 312, the biasing member 358 can be positioned between the proximal portion of the first base 310 and a portion of the second base 312. The proximal portion of the biasing member 358 can engage the inner surface of the proximal wall 340, and the distal portion of the biasing member 358 can engage the an arm 350 of the second base 312. The biasing member 358 can be positioned to urge the first base 310 toward the distal portion of the cover member 304.

In a first configuration, the first base 310 is positioned within the distal portion of the second base 312. In some embodiments, the biasing member 358 urges the first base 310 toward the distal portion of the second base 312, as illustrated in FIG. 4.

Figure 6:
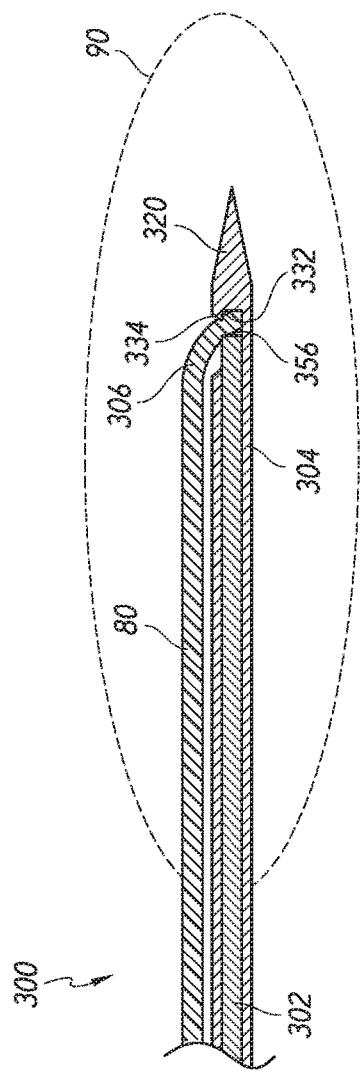

In the first configuration, the distal portion of the piston 302 can compress or pinch the distal portion of the thread 80 against the cover member cavity. For example, the distal end surface of the piston 302 can compress or pinch the distal portion of the thread 80 against the first thread engagement surface 332. The first base 310 or piston 302 can comprise a length so that the second thread engagement surface 356 is separated or spaced apart from the first thread engagement surface 332 by a first distance in the first configuration. The first distance can be less than the diameter of the thread 80, such that a portion of the thread 80 is pinched or engaged between the piston 302 and cover member 304, as illustrated in FIG. 6. In the first configuration, a portion of the piston 302 extends across a portion of the cover member 304 having the aperture 334, thereby obstructing a portion of the aperture 334.

In the second configuration, the first base 310 is positioned within the proximal portion of the second base 312, as illustrated in FIG. 5. In some embodiments, the first base can be urged toward the proximal portion of the second base 312 in the second configuration. To urge the first base 310 toward the second base 312, the biasing member 358 can be urged or compressed, between the first and second bases 310, 312.

In the second configuration, the distal portion of the piston 302 can be separated, or retracted from, an inner surface of the cover member 304. The second thread engagement surface 356 can be retracted from the first thread engagement surface 332. In the second configuration, the second thread engagement surface 356 can be separated or spaced apart from the first thread engagement surface 332 by a second distance. The second distance can be approximately equal to or greater than the diameter of the thread 80, such that the piston 302 and cover member 304 separate from the thread 80, as illustrated in FIG. 6.

To use the insertion device 300, the first base 310 can be moved relative to the second base 312, such that the second thread engagement surface 356 is separated from the first thread engagement surface 332. The first base 310 can be retracted to separate the second thread engagement surface 356 from the first thread engagement surface 332. A portion of the thread 80 can be positioned to extend through the aperture 334 of the cover member, and between the piston 302 and the cover member 304. To retain a distal portion 306 of the thread 80 with the insertion device 300, the first base 310 can be moved relative to the second base 312, such that the second thread engagement surface 356 is directed toward the first thread engagement surface 332, e.g., the first configuration. In the first configuration, a portion of the thread 80 is engaged between the first thread engagement surface 332 and the second thread engagement surface 356, as illustrated in FIG. 6.

To retain the proximal portion of the thread 80 along the cover member 304, the fastener 314 can be coupled to the insertion device 300. The fastener 314 can be coupled to the insertion device 300 to extend around an outer surface of the cover member 304 and the thread 80. The fastener 314 can engage the thread 80 between an inner surface of the fastener 314 and an outer surface of the cover member 304. With the distal portion 306 of the thread 80 retained between the piston 302 and the cover member 304, and the proximal portion of the thread 80 retained between the fastener 314 and the outer surface of the cover member 304, the thread 80 can be positioned with its longitudinal axis aligned with respect to the longitudinal axis of the cover member 304.

In the first configuration, the insertion device 300 can be directed toward a patient so that the tip portion 320 of the cover member pierces the patient's skin 90 and permits further movement of the insertion device 300 into the patient. An opening can be created through the patient's skin by a separate device to permit insertion of the cover member 304. The insertion device 300 can be moved relative to a longitudinal and transverse axis of the device to position the thread 80 at a specific location. Movement of the insertion device 300 can comprise inserting, retracting, pitching, rolling, and/or yawing relative to the longitudinal and transverse axis and the patient.

Figure 7:
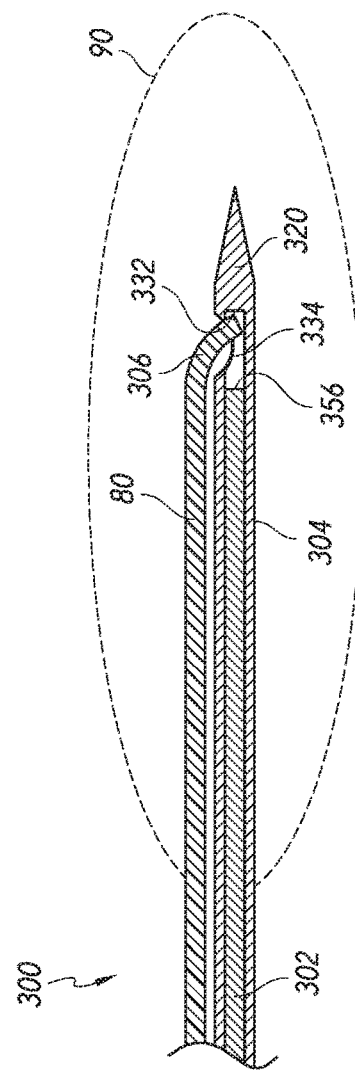

To release the thread 80, the insertion device 300 can be moved to the second configuration. To release the thread 80, the first base 310 can be retracted to retract the second thread engagement surface 356 from the first thread engagement surface 332, as illustrated in FIG. 7. To retract the first base 310, the physician can place a first finger, e.g., a thumb, on the outer surface of the proximal wall 340, and one or more finger, e.g., an index and middle finger, on the flanges 354. The physician can then move the first base 310 toward the second base 312. In the second configuration, the distal portion 306 of the thread 80 is permitted to move through the aperture 334 and out of the cavity of the cover member 304.

The fastener 314 can be removed from the insertion device 300 release a portion of the thread 80. The fastener 314 can be removed before or after moving the insertion device 300 to the second configuration. The thread 80 can be separated from the fastener 314 and the insertion device 300 can be moved to the second configuration.

Figure 8:
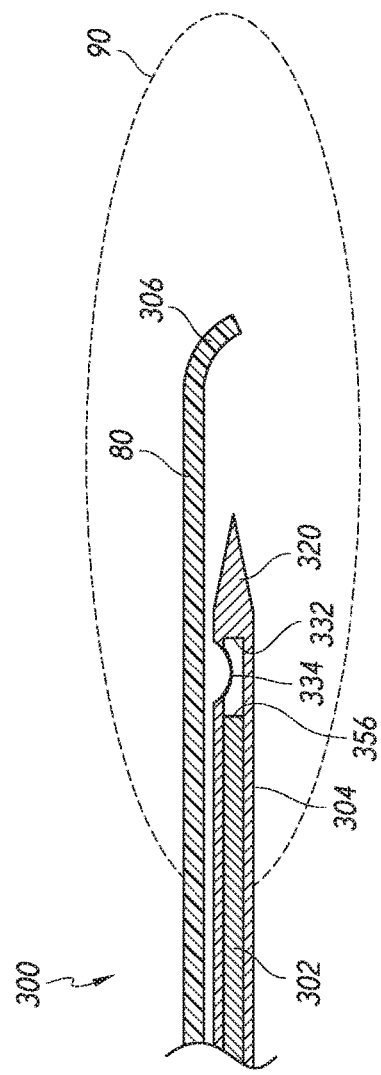

To implant the thread 80, the insertion device 300 can be retracted from the thread 80, as illustrated FIG. 8. The insertion device 300 can be retracted until the cover member 304 is withdrawn from the patient. Any portion of the thread 80 that remains extending through the surface of the patient's skin can be separated or cut so that the remaining portion is entirely within the patient's skin.

Referring now to FIGS. 9-13, another embodiment of the insertion device can be configured to attach with or otherwise engage a distal portion of the thread to "push" the thread to a desired position in situ and then to disengage with the distal portion of the thread from the device after the thread reaches the desired position. For example, FIGS. 9-13 illustrate an insertion device 400 that can comprise a component that can be moved to separate a thread from the insertion device 400. The insertion device 400 can comprise a cover member 402 and a piston 404. Similar to the insertion device 300, the piston 404 can be moved relative to the cover member 402 in order to detach or disengage the distal portion 406 of a HA thread 80 from the insertion device 400.

The insertion device 400 can also comprise a first base 410 and a second base 412. The first base 410 can comprise a proximal wall 422, and the second base 412 can comprise on or more flanges 426. These and other components of the insertion device 400 can share various features and aspects with the components discussed above with respect to the insertion device 300, as shown in FIGS. 2-5. Accordingly, features and aspects of these components are already discussed above with respect to the insertion device 300 and all of the details will not be repeated herein for brevity.

Referring to FIG. 9, the cover member 402 comprises a proximal portion and a distal portion. The cover member 402 comprises a longitudinal axis that extends between the proximal and distal portions. The proximal and distal portions can comprise a tubular shape along a longitudinal length of cover member 402. A cross-sectional profile transverse to the longitudinal axis of the cover member 402 can comprise a circle, oval, regular or irregular polygon, square, and/or rectangle shape. The shape or size can vary along the length or width of the cover member 402. In some embodiments, the cover member 402 can comprise a hypodermic tube.

The distal portion of the cover member 402 can comprises an outer surface that tapers toward a distal end. The distal portion can comprise a distal end surface 408 that is transverse to the longitudinal axis of the cover member 402, e.g., a bevel. The distal end surface 408 can permit the cover member 402 to pierce the patient's skin or tissue to allow insertion of the cover member 402. The distal end can comprise an outer surface that is rounded or blunt. A round or blunt surface can permit insertion of the cover member through an opening of the patient causing damage to the patient's tissue.

The cover member 402 comprises passage that extends between tubular proximal and distal portions of the cover member 402. The passage can extend from the proximal portion through the distal portion of the cover member 402. The portion of the cover member 402 comprising the passage can have a cross-sectional profile, transverse to the cover member longitudinal axis, having a circle, oval, regular or irregular polygon, square, and/or rectangle shape. The inner surface of the cover member that forms the cavity can have a profile that corresponds to an outer surface of the piston 404 configured to extend through the cavity. The shape or size of the cavity can vary along the length or width of the cavity. The cavity is configured to permit the piston 404 to extend within the cavity and move along the longitudinal axis of the cover member 402.

The cover member 402 can comprise an aperture 414 configured to permit a portion of the thread 80 to extend toward the cavity. The aperture 414 can extend through the distal portion of the cover member 402. Referring to FIG. 10, the aperture 414 can extend through a distal portion of the cover member 402. The aperture 414 can extend transverse to the longitudinal axis of the cover member 402. The distal portion of the cover member 402 can comprise a notch 416 that extends from an edge of the aperture 414. The notch 416 can extend toward proximal portion of the cover member 402, as illustrated in FIG. 10A. The notch 416 can advantageously accommodate the distal portion 406 of the thread 80 therewithin during the injection procedure to minimize frictional resistance against the distal portion 406 during advancement into and within the skin 90. Accordingly, in some embodiments, the sharp edge of the distal end surface or bevel 408 can be replaced by a blunt-faced notch against which the distal portion 406 of the thread 80 can press without tending to cut or slice the distal portion 406 of the thread 80 prematurely.

The notch can have a width, transverse to the longitudinal axis of the cover member 402, that is approximately equal to or greater than a diameter of the thread 80. The width of the notch 416 can taper toward the proximal portion of the cover member 402. A wall portion of the cover member 402 that forms the notch 416 can have a cross-sectional thickness that tapers toward the notch 416. The tapered wall portion of the cover member 402 can comprise a bevel or other sharp edge configured to separate or sever a portion of a thread moved into the bevel or other sharp edge of the notch 416. The notch 416 can separate or sever a thread 80 that is moved along or around the longitudinal axis of the cover member 402.

The piston 404 can be coupled to the first base 410 and can extend within the cavity of the cover member 402. The piston 404 can comprise a shaft, a rod, and/or a plate having a longitudinal axis between a proximal portion and a distal portion. The distal portion of the piston 404 can extend within the cavity of the cover member 402 and can move along a longitudinal axis of the cover member 402. The distal portion of the piston 404 can comprise a thread attachment surface 420. The thread attachment surface 420 can comprise an outer surface of the piston 404 to which the thread 80 is attached. However, in some embodiments, the thread 80 can be adhered or coupled to a portion of the cover member 402. The thread 80 can be adhered to the thread attachment surface 420 using an adhesive such as, for example, glue, tape, or other solutions that can be broken or dissolved in situ.

A cross-sectional profile transverse to the longitudinal axis of the piston 404 can comprise a circle, oval, regular or irregular polygon, square, and/or rectangle shape. The shape or size can vary along the length or width of the piston 404. The outer surface of the piston 404 can have a profile that corresponds to the cavity of the cover member 402, and can be engaged against the inner surface of the cover member 402. The outer surface of the piston 404 can comprise a smaller profile shape than the inner surface of the cover member 402.

The piston 404 can extend from the distal most surface of the first base 410 toward the aperture 414 of the cover member 402. The piston 404 can have a length, such that the distal portion of the piston 404 is proximal to the notch 416 and/or the aperture 414, or extends along the notch 416 and/or the aperture 414. The distal portion of the piston 404 can have a distal end surface 418 that is transverse to the longitudinal axis of the piston 404, e.g., a bevel. The distal end surface 418 of the piston 404 can correspond with the distal end surface of the cover member 402.

In a first configuration, the distal portion of the piston 404 can be positioned adjacent to a distal portion of the cover member 402. The first base 410 can be positioned within the distal portion of the second base 412, in the first configuration, as illustrated in FIG. 4. The biasing member can urge the first base 410 toward the distal portion of the second base 412.

The piston 404 can comprise a length so that the thread attachment surface 420 is positioned adjacent to the distal portion of the cover member 402 in a first configuration or a second configuration. In some embodiments, the distal portion of the piston 404 can extend along the notch 416, such that the distal end surfaces of the piston 404 and the cover member 402 are aligned in the first configuration. For example, the distal end surfaces or bevels 418, 408 of the piston 404 and the cover member 402, respectively, can be aligned around respective longitudinal axes such that the respective distal end surfaces or bevels 418, 408 form a common transverse plane.

In the first configuration a portion of the thread 80 can be adhered to the insertion device 400. In some embodiments, the thread 80 can be adhered to the cover member 402 or the piston 404. The distal portion 406 of the thread 80 can be adhered to the thread attachment surface 420, as illustrated in FIG. 11. The distal portion 406 of the thread 80 can be adhered to the piston 404 by tying the thread to the piston, extending a portion of the thread 80 through an aperture, groove, or notch of the piston 404, and/or engaging the thread 80 between portions of the piston 404. The thread 80 can be adhered to the thread attachment surface 420 so that a portion of the thread extends through the notch 416, thereby preventing movement of thread 80 relative to the longitudinal axis of the cover member 402, e.g., axial or transverse to the longitudinal axis.

The proximal portion of the thread 80, which extends from the aperture 414, can be positioned along the cover member 402. The thread 80 can be positioned so that a longitudinal length of the proximal portion of the thread extends along a longitudinal length of the cover member 402. The portion of the thread that extends from the aperture 414 can be engaged against the outer surface of the cover member 402. To retain the proximal portion of the thread 80 along the cover member 402, the fastener 430 can be coupled to the insertion device 400. The fastener 430 can be coupled to the insertion device 400 to engage the thread 80 between the fastener 430 and the outer surface of the cover member 402.

In the second configuration, the piston 404 can be moved, relative to the cover member 402, to separate the thread 80 from the insertion device 400. The first base 410 can be positioned within the proximal portion of the second base 412, in the second configuration, as similarly illustrated in FIG. 5. In some embodiments, the first base can be moved toward the proximal portion of the second base 412 in the second configuration. To move the first base 410 toward the second base 412, the biasing member can be urged or compressed between the first and second bases 410, 412.

In the second configuration, the piston 404 can be moved, relative to the cover member 402, to separate the thread 80 from the insertion device 400. To separate the thread 80, the distal portion of the piston 404 can be retracted proximal to the aperture 414 of the cover member 402, or advanced distal to the aperture 414 of the cover member 402. When the piston 404 is moved, the thread 80 engages against the cover member 402, e.g., a surface of the notch 416 and/or the aperture 414. The engagement of the thread 80 against the cover member 402, at the notch 416 or aperture 414, prevents the thread 80 from moving with the piston 404 and can cause the thread 80 to separate from the thread attachment surface 420, as illustrated in FIG. 12. Engagement of the thread 80 against the cover member 402 can separate the proximal and distal portions of the thread 80.

The insertion device 400 can be directed toward the patient in the first configuration, so that the distal end surface of the cover member 402 pierces the skin 90 of the patient and permit further movement of the insertion device 400 into the patient. An opening can be created through the patient's skin by a separate device to permit movement of the insertion device 400 through the skin 90. The insertion device 400 can be moved, relative to a longitudinal and transverse axis of the device, to position the thread 80 at a specific location. In some methods, movement of the insertion device 400 can comprise inserting, retracting, pitching, rolling, and/or yawing relative to the longitudinal and transverse axis and the patient.

The insertion device 400 can be moved to the second configuration to separate the distal portion 406 of the thread 80 from the insertion device 400. To separate the thread 80, the distal portion of the piston 404 can be retracted proximal to the aperture 414 of the cover member 402. When the piston 404 is moved, the thread 80 can engage the cover member 402 at the notch 416. Engagement of the thread 80 against the cover member 402 can prevent the thread 80 from moving with the piston 404 and cause the thread 80 to separate from the thread attachment surface 420, as illustrated in FIG. 12.

To release the proximal portion of the thread 80, the fastener 430 can be removed from the insertion device 400. The fastener 430 can be removed before or after moving the insertion device 400 to the second configuration. The thread 80 can be separated from the fastener 430 and the insertion device 400 can be moved to the second configuration.

To implant the thread 80, the insertion device 400 can be retracted from the thread 80, as illustrated FIG. 13. The insertion device 400 can be retracted until the cover member 402 is withdrawn from the patient. Any portion of the thread 80 that remains extending through the surface of the patient's skin can be separated or cut so that the remaining portion is entirely within the patient's skin.

Referring now to FIGS. 14-20, another embodiment of the insertion device can be configured to pinch, compress, or otherwise engage a distal portion of the thread to "push" the thread to a desired position in situ and then to disengage with or sever the distal portion of the thread from the device after the thread reaches the desired position. The insertion device can comprise a thread that is pinched or crimped at an end portion of a cover member and separable therefrom by moving a portion of the insertion device to open the pinched or crimped end portion or to sever the thread from the end portion. For example, FIGS. 14-20 illustrate an insertion device 450 that comprises a cover member 452 and a piston 454 that can be used to engage and disengage with a distal portion 458 of a HA thread 80.

Further, the insertion device 450 can also comprise a first base 460 and a second base 462 coupled to the respective ones of the cover member 452 and the piston 454 in order to actuate the insertion device 450. The piston 454 and first base 460 can be moved relative to the cover member 452 and second base 462 to cut, sever, or separate the distal portion 458 the thread 80 from the cover member 452. These and other components of the insertion device 450 can share various features and aspects with the components discussed above with respect to the insertion devices 300, 400. Accordingly, features and aspects of these components are already discussed above with respect to the insertion devices 300, 400 and all of the details will not be repeated herein for brevity.

Referring to FIG. 14, the cover member 452 can comprise a proximal portion and a distal portion. The cover member 452 comprises a longitudinal axis that extends between the proximal and distal portions. The proximal and distal portions can comprise a tubular shape along a longitudinal length of cover member 452. A cross-sectional profile transverse to the longitudinal axis of the cover member 452 can comprise of a circle, oval, regular or irregular polygon, square, and/or rectangle shape. The shape or size can vary along the length or width of the cover member 452. In some embodiments, the cover member 452 can comprise a hypodermic tube.

The cover member 452 can comprise a cavity that extends between proximal and distal portions of the cover member 452. The cavity can extend from the proximal portion through a distal end surface of the cover member 452. The portion of the cover member 452 comprising the cavity can have a cross-sectional profile, transverse to the cover member longitudinal axis, having a circle, oval, regular or irregular polygon, square, and/or rectangle shape. The inner surface cross-sectional profile of the cover member can comprise a profile that corresponds to an outer surface of the piston 454. The shape or size of the cavity can vary along the length or width of the cavity. The cavity can permit the piston 454 to extend within the cavity and move along the longitudinal axis of the cover member 452.

The distal portion of the cover member 452 can comprise an opening configured to permit a thread to extend into the cavity. The opening can extend through the proximal or distal portion of the cover member 452. The opening can be an aperture 464 that extends through the distal end surface of the cover member 452, as illustrated in FIG. 14. In such embodiments, the piston 454 can be urged distally to spread or force open the aperture 464 in order to release the distal portion 458 of the thread 80. However, in some embodiments, the aperture 464 can also be positioned to extend through a sidewall of the cover member 452, transverse to the longitudinal axis of the cover member 452, as illustrated in FIG. 15. As discussed further below, in such embodiments, the piston 454 can be used to sever the distal portion 458 of the thread 80 from connection with the insertion device 450.

The aperture 464 can be positioned to provide a passage from the outer surface of the cover member into the cavity. The aperture 464 can be positioned proximally of a distal portion of the cover member 452. The cavity of the cover member 452 can extend distal to the aperture 464. The aperture 464 can permit a portion of a thread 80 to extend into the cavity of the cover member 452. The thread 80 can extend through the aperture 464 and into the cavity in a direction toward the proximal portion of the cover member 452, e.g., FIG. 14, or can extend into the cavity in a direction toward the distal portion of the cover member 452, e.g., FIG. 18.

A portion of the thread 80 that extends into the cavity can be coupled to the cover member 452. The portion of the thread 80 can be coupled to the cover member 452 by engaging the cover member 452 against the thread 80. A portion of the cover member 452 that extends along the thread 80 can be moved to engage in the thread 80. The cover member 452 can be moved to engage the thread 80 by compressing, bending, and/or crimping. In some embodiments, a thread engagement portion 466 of the cover member can be crimped, pinched, and/or biased toward the cavity, such that an inner surface of the cover member extends into the cavity to engage in the thread 80. In some embodiments, the cover member 452 can be coupled to the thread 80 using an adhesive such as, for example, glue, tape, or other solutions that can be broken or dissolved in situ.

The distal portion of the cover member 452 can comprise a tip portion 470 having a tapered outer surface. The tip portion 470 can extend from the aperture 464 or a distal-most surface of the cover member cavity toward the distal portion of the cover member 452. The tip portion 470 can comprise an outer surface that tapers toward the distal portion of the cover member 452. The distal portion of the cover member 452 can comprise a distal end surface 472 that is transverse to the longitudinal axis of the cover member 452, e.g., a needle point or bevel. The distal end surface 472 can permit the cover member 452 to pierce the patient's skin or tissue to allow insertion of the cover member 452. The tip portion 470 can comprise an outer surface that is rounded or blunt. A round or blunt surface can prevent damage to the patient's tissue during insertion of the cover member.

The piston 454 can extend within the cavity of the cover member 452. The piston 454 can comprise a shaft, a rod, and/or a plate having a longitudinal axis between a proximal portion and a distal portion. The distal portion of the piston 454 can extend within the cavity of the cover member 452 and is configured to move along a longitudinal axis of the cover member 452. In the embodiment of FIG. 14, the distal portion of the piston 454 can comprise a thread detachment portion 474. The thread detachment portion 474 can comprise a distal end surface of the piston 454 and can be used to urge open the aperture 464 to release the distal portion 458 of the thread 80. However, in the embodiment shown in FIGS. 15-20, the thread detachment portion 474 can be configured to sever the distal portion 458 of the thread 80 from its coupling with the insertion device 450, as discussed below.

A cross-sectional profile transverse to the longitudinal axis of the piston 454 can comprise a circle, oval, regular or irregular polygon, square, and/or rectangle shape. The shape or size can vary along the length or width of the piston 454. The outer surface of the piston 454 can have a profile that corresponds to the cavity of the cover member 452, and can be engaged against the inner surface of the cover member 452. The outer surface of the piston 454 can comprise a smaller profile shape than the inner surface of the cover member 452.

The piston 454 can extend from the distal most surface of the first base 460 toward the aperture 464 of the cover member 452. The piston 454 can have a length, such that the distal portion of the piston 454 is proximal to the aperture 464, or extends along the aperture 464. The piston 454 can have distal portion with an outer surface that is configured to sever a thread 80. The outer surface can taper toward the distal portion of the piston 454. The distal portion can comprise a distal end surface that is transverse to the longitudinal axis of the piston 454, e.g., a needle point or bevel.

The insertion device 450 can be configured with the piston 454 coupled to the first base 460, and the cover member coupled to the second base 462. The first base 460 can comprise a proximal portion and a distal portion, opposite the proximal portion, and a longitudinal axis between the proximal and distal portions. The piston 454 can be coupled to the first base 460, such that the distal portion of the piston 454 extends from the distal portion of the first base. The proximal portion of piston can extend into the distal portion of the first base 460, as illustrated in FIG. 16.

The distal portion of the first base 460 can comprise an outer cross-sectional profile transverse to the longitudinal axis. The distal portion of the first base 460 is configured to be positioned within a cavity of the second base 462. A cross-sectional outer surface of the first base 460 can be approximately equal to or less than a cross-sectional inner surface profile of the second base 462.

The proximal portion of the first base 460 can comprise an outer surface with a reduced cross-sectional profile, relative to the distal portion of the first base 460. The outer surface of the first base 460, between the reduced cross-sectional profile of the proximal portion and the distal portion, can form a ledge 480 that extends radially outward from the longitudinal axis of the first base 460.

The proximal portion of first base 460 can be engaged by a portion of the physician's hand, e.g., the physician's palm or thumb. The proximal portion of the first base 460 can comprise a proximal-most outer surface with a concave portion that can be engaged or grasped by a portion of the physician's hand.

The distal portion of the first base 460 can be engaged against a biasing member 482. A distal portion of the first base 460 can have an outer cross-sectional profile that is equal to or less than an inner cross sectional profile of a biasing member 482, such that a portion of the biasing member 482 extends around the distal portion of the first base 460. A distal portion of the first base 460 can have a groove or ridge that can be engaged by a portion of the biasing member 482. The biasing member 482 can be a spring and/or a piston.

The second base 462 can comprise a proximal portion and a distal portion. An inner cavity can extend from the proximal portion to toward the distal portion of the second base 462. The cover member 452 can be coupled to the second base 462, such that the distal portion of the cover member 452 extends from the distal portion of the second base 462. The distal portion of the second base 462 can be coupled to the proximal portion of the cover member 452, such that the cavity of the second base 462 is open to the cavity of the cover member 452.

The cavity of the second base 462 and the cover member 452 can form a passage that extends from the second base 462 to the distal aperture 464 of the cover member 452. The cavity of the second base 462 can permit a portion of the first base 460 and/or the piston 454 to be positioned therein. The cavity of the second base 462 and the cover member 452 can permit portions of the first base 460 and the piston 454 to move therein.

The proximal portion of second base 462 can comprise a proximal wall 484 comprising an opening between the cavity and outer surface of the second base 462. The opening can permit a portion of the first base 460, configured to be engaged by a portion of the physician's hand, to extend through the proximal wall 484.

The outer surface of the second base 462 can comprise a flange 486 configured to permit a physician to grasp the second base 462 with a hand or finger. The flange can extend from the outer surface, transverse to the longitudinal axis of the second base 462. The flange 486 can be a proximal portion of the second base 462 comprising a ledge, lever, protrusion, knob, ring, groove, and/or ridge. The insertion device 450 can comprise first and second flanges 486. The first and second flanges 486 can extend laterally away from the outer surface of the second base 462 in different directions. The first and second flanges 486 can extend from the outer surface of the second base 462 in opposing directions. In some methods, one or more finger of a physician, e.g., an index finger and a middle finger, can be engaged against one or more flange 486.

A resilient biasing member 482, e.g., a spring, can be configured to bias the first and second bases 460, 462 relative to each other. The biasing member 482 can comprise a proximal portion and a distal portion. The proximal portion of the biasing member 482 can engage the first base 460, and the distal portion of the biasing member 482 can engage the second base 462.

The biasing member 482 can be positioned between the first base 460 and the second base 462 to urge the first base 460 toward the proximal portion of the second base 462. To urge the first base 460 toward the proximal portion of the second base 462, the biasing member 482 can be positioned in the cavity of the second base 462, between the distal portion of the first base 460 and a portion of the second base 462. The biasing member 482 can be positioned between the distal portion of the first base 460 and the distal portion of the second base 462 to urge the ledge 480 of the first base 460 toward the proximal wall 484 of the second base 462.

In a first configuration, the first base 460 can be positioned within the proximal portion of the second base 462. The first base and second base can be positioned so that a distal-most outer surface of the first base 460 is separated from the an inner surface of the cavity of the second base 462. The first base 460 can be urged toward the second base 462 by the biasing member 482, such that the ledge 480 is engaged against the proximal wall 484, as illustrated in FIG. 16.

In the first configuration, the distal portion of the piston 454 can be positioned adjacent to a distal portion of the cover member cavity. A length of the first base 460 or piston 454 can be configured so the thread detachment portion 474 of the piston is adjacent to the thread engagement portion 466 of the cover member. The thread detachment portion 474 can be positioned adjacent to the aperture 464, and in the embodiment of FIGS. 15-20, the thread detachment portion 474 does not extend across the aperture 464.

In the first configuration, a distal portion 458 of the thread 80 can be inserted into the cavity of the cover member 452, and the cover member can be engaged against the thread 80, as illustrated in FIGS. 14 and 18. The cover member 452 can be engaged with the thread by compressing, pinching, or crimping the thread engagement portion 466 toward the thread 80 so that the thread is compressed, pinched, or crimped by the thread engagement portion 466 of the cover member 452.

The proximal portion of the thread 80, which extends from the aperture 464, can be positioned along the cover member 452. The thread 80 can be positioned so that the proximal portion of the thread extends along a longitudinal axis of the cover member 452. The portion of the thread that extends from the aperture 464 can be engaged against the outer surface of the cover member 452. To retain the proximal portion of the thread 80 along the cover member 452, the fastener 488 can be coupled to the insertion device 450. The fastener 488 can be coupled to the insertion device 450 to engage the thread 80 between the fastener 488 and the outer surface of the cover member 452.

In the second configuration, the piston 454 can be moved, relative to the cover member 452, to cut, sever, or separate the distal portion 458 of the thread 80 from the insertion device 450. The piston 454 can be moved by urging the distal portion of the first base 460 toward distal portion of the second base 462. When the first base 460 is moved toward the second base 462 the ledge 480 can be separated from the proximal wall 484, and the biasing member 482 can be compressed between the distal portion of the first and second bases 460, 462.

In the second configuration, a distal portion of the piston 454 can extend across the portion of the cover member comprising the aperture 464. The distal portion of the piston 454 can extend across the portion of the cover member cavity comprising the thread engagement portion 466. When the piston 454 is moved into toward thread engagement portion 466, the thread detachment portion 474 can engage and move the cover member 452 to cut, sever, or separate the distal portion 458 of the thread 80 from the insertion device 450. In some embodiments, the thread detachment portion 474 can engage and move the thread 80 from the insertion device 450. However, in some embodiments, an end portion of the thread 80 can be severed from the remainder of the thread and remain crimped within the thread engagement portion 466. Thus, a portion of the thread 80 can be sacrificed to when the thread 80 is cut from the insertion device 450.

The insertion device 450 can be directed toward the patient in the first configuration, so that the distal end surface of the cover member 452 pierces the skin 90 of the patient and permits movement of the insertion device 450 into the patient. An opening can be created through the patient's skin by a separate device to permit movement of the insertion device 450 through the skin 90. The insertion device 450 can be moved, relative to a longitudinal and transverse axis of the device, to position the thread 80 at a specific location. In some methods, movement of the insertion device 450 can comprise inserting, retracting, pitching, rolling, and/or yawing relative to the longitudinal and transverse axis and the patient.

The insertion device 450 can be moved to the second configuration to cut, sever, or separate the distal portion 458 of the thread 80 from the insertion device 450. To cut the thread 80, the distal portion of the piston 454 can be moved toward the aperture 464 of the cover member 452. The distal portion of the piston 454 can be moved across the aperture 464 so that the thread detachment portion 474 engages the portion of thread 80 that extends through the aperture 464. As the distal portion of the piston 454 bypasses the aperture 464, the portion of thread 80 that extends through the aperture 464 can be severed or separated from the cover member 452, as illustrated in FIG. 19.

The first base 460 can be moved into the second base 462 to move the piston 454 toward the aperture 464. To move the first base 460, the physician can place a first finger, e.g., a thumb, on the proximal outer surface of the first base 460, and one or more finger, e.g., an index and middle finger, on the flanges 486. The physician can then move the first base 460 toward the second base 462.

To release the proximal portion of the thread 80, the fastener 488 can removed from the insertion device 450. The fastener 488 can be removed before or after moving the insertion device 450 to the second configuration. The thread 80 can be separated from the fastener 488 and the insertion device 450 can be moved to the second configuration.

To implant the thread 80, the insertion device 450 can be retracted from the thread 80, as illustrated FIG. 20. The insertion device 450 can be retracted until the cover member 452 is withdrawn from the patient. Any portion of the thread 80 that remains extending through the surface of the patient's skin can be separated or cut so that the remaining portion is entirely within the patient's skin.

Referring now to FIGS. 21-24, another embodiment of the insertion device can be configured to pinch, compress, or otherwise engage a distal portion of the thread to "push" the thread to a desired position in situ and then to disengage with or sever the distal portion of the thread from the device after the thread reaches the desired position. In some embodiments, a thread can extend through a portion of a cover member of an insertion device, and a portion of the insertion device can be moved to cut, sever, or separate the thread from the cover member. For example, FIGS. 21-24 illustrate an insertion device 500 can comprise a cover member 502 and a piston 504 that can engage with and disengage a distal portion 506 of a HA thread 80 from the insertion device 500. Further, the insertion device 500 can comprise a first base 510 and a second base 512 coupled to the respective ones of the cover member 502 and the piston 504 in order to actuate the insertion device 500. These and other components of the insertion device 500 can share various features and aspects with the components discussed above with respect to the insertion devices 300, 400, 450. Accordingly, features and aspects of these components are already discussed above with respect to the insertion devices 300, 400, 450 and all of the details will not be repeated herein for brevity.

Referring to FIG. 21, the cover member 502 can comprise a proximal portion and a distal portion. The cover member 502 can comprise a longitudinal axis that extends between the proximal and distal portions. The proximal and distal portions can comprise a tubular shape along a longitudinal length of cover member 502. An outer cross-sectional profile transverse to the longitudinal axis of the cover member 502 can comprise a circle, oval, regular or irregular polygon, square, and/or rectangle shape. The shape or size can vary along the length or width of the cover member 502. In some embodiments, the cover member 502 can comprise a hypodermic tube.

The distal portion of the cover member 502 can comprises an outer surface that tapers toward a distal end. The distal portion can comprise a distal end surface 514 that is transverse to the longitudinal axis of the cover member 502, e.g., a bevel. The distal end surface 514 can permit the cover member 502 to pierce the patient's skin or tissue to allow insertion of the cover member 502. The distal portion can comprise an outer surface that can be rounded or blunt. A round or blunt surface can permit insertion of the cover member through an opening of the patient causing damage to the patient's tissue.

The cover member 502 can comprise cavity 516 that extends between tubular proximal and distal portions of the cover member 502. The passage can extend from the proximal portion toward the distal portion of the cover member 502. The portion of the cover member 502 comprising the cavity can have a cross-sectional profile, transverse to the cover member longitudinal axis, having a circle, oval, regular or irregular polygon, square, and/or rectangle shape. The inner surface of the cover member that forms the cavity can have a profile that corresponds to an outer surface of the piston 504 configured to extend through the cavity. The shape or size of the cavity can vary along the length or width of the cavity. The cavity is configured to permit the piston 504 to extend within the cavity and move along the longitudinal axis of the cover member 502.

The cover member 502 can comprise an aperture 520 configured to permit a portion of the thread 80 to extend into the cavity. The aperture 520 can extend transverse to the longitudinal axis of the cover member 502. The cover member 502 can comprise first and second apertures that extend through opposing outer surfaces of the cover member. The opposing apertures can be positioned to create a passage that extends across the outer surfaces of the cover member 502 and intersects the cavity.

The piston 504 can be coupled to the first base 510, and the cover member 502 can be coupled to the second base 512. The piston 504 is configured to extend within the cavity of the cover member 502, from the first base 510 toward the aperture 520 of the cover member 502.

In a first configuration, the distal portion of the piston 504 can be positioned adjacent to a distal portion of the cover member 502. The first base 510 can be positioned within the second base 512, in the first configuration, as illustrated in FIG. 4. A longitudinal length of the first base 510 and/or piston 504 can be configured so that a distal portion of the piston 504 is adjacent to the distal portion of the cover member 502. In the first configuration, the piston 504 can be proximal to the aperture 520, but does not extend across aperture 520.

In the first configuration a portion of the thread 80 can be coupled to the insertion device 500. The thread 80 can be coupled to the cover member 502. The distal portion of the thread 80 can extend through the aperture 520 and be adhered to the cover member 502 using an adhesive such as, for example, glue, tape, or other solutions. Thus, the thread 80 can be extended through the first and second apertures and be coupled to the cover member 502, as illustrated in FIG. 21. In some embodiments, the thread 80 can be adhered to the piston 504, or engaged between the piston 504 and the cover member 502, proximal to the aperture 520. A distal portion of the piston 504 can be engaged against the distal portion of the thread 80 extending through the aperture 520.

The proximal portion of the thread 80, which extends from the aperture 520, can be positioned along the proximal portion of the cover member 502, and can be engaged against the outer surface of the cover member 502 To retain the proximal portion of the thread 80 along the cover member 502, the fastener 530 can be coupled to the insertion device 500. The fastener 530 can be coupled to the insertion device 500 to engage the thread 80 between the fastener 530 and the outer surface of the cover member 502.

In the second configuration, the piston 504 can be moved, relative to the cover member 502, to cut, sever, or separate the thread 80 from the insertion device 500. The piston 504 can be moved by urging the distal portion of the first base 510 toward distal portion of the second base 512. When the first base 510 is moved toward the second base 512, the distal portion of the piston 504 can extend across the portion of the cover member comprising the aperture 520.

The insertion device 500 can be directed toward the patient in the first configuration, so that the distal end surface of the cover member 502 pierces the skin 90 of the patient and permits further movement of the insertion device 500 into the patient. An opening can be created through the patient's skin by a separate device to permit movement of the insertion device 500 through the skin 90.

The insertion device 500 can be moved to the second configuration to cut, sever, or separate the distal portion 506 of the thread 80 from the insertion device 500. To separate the thread 80, the distal portion of the piston 504 can be moved toward the aperture 520 of the cover member 502. As the piston 504 moves across the aperture 520, the distal portion 506 of the thread 80 that extends through the aperture 520 will be contacted, stretched, and eventually severed by the piston 504, as illustrated in FIG. 23.

To release the proximal portion of the thread 80, the fastener 530 is removed from the insertion device 500. The fastener 530 can be removed before or after moving the insertion device 500 to the second configuration. The fastener 530 can be configured to permit movement of the thread 80 between the fastener 530 and cover member 502. To permit movement of the thread 80 between the fastener 530 and cover member 502, a distance between the inner surface of the fastener 530 and an outer surface of the cover member 502 can be equal to or greater than the outer surface cross-section profile of the thread.

To implant the thread 80, the insertion device 500 can be retracted from the thread 80, as illustrated FIG. 24. As the insertion device 500 is retracted, the fastener is removed from the proximal portion of the thread. The insertion device 500 can be retracted until the cover member 502 is withdrawn from the patient. Any portion of the thread 80 that remains extending through the surface of the patient's skin can be separated or cut so that the remaining portion is entirely within the patient's skin.

Referring now to FIGS. 25-28, another embodiment of the insertion device can be configured to pinch, adhere to, or otherwise engage a distal portion of the thread to "push" the thread to a desired position in situ and then to disengage with or eject the thread or sever the distal portion of the thread from the device after the thread reaches the desired position. FIGS. 25-28 illustrate an insertion device 550 that comprises a piston that is moveable relative to a cover member to eject, sever, or separate at least a portion of a thread coupled along an inner surface cover member to cause the thread to be released from the cover member. The insertion device 550 can comprise a cover member 552 and a piston 554 that can engage with and disengage a distal portion 506 of a HA thread 80 from the insertion device 550. Further, the insertion device 550 can also comprise a first base 560 and a second base 562 coupled to the respective ones of the cover member 552 and the piston 554 in order to actuate the insertion device 550. These and other components of the insertion device 550 can share various features and aspects with the components discussed above with respect to the insertion devices 300, 400, 450, 500. Accordingly, features and aspects of these components are already discussed above with respect to the insertion devices 300, 400, 450, 500 and all of the details will not be repeated herein for brevity.

Referring to FIG. 25, the cover member 552 can comprise a proximal portion and a distal portion. The cover member 552 can comprise a longitudinal axis that extends between the proximal and distal portions. A portion of the proximal and distal portions can comprise a tubular shape along a longitudinal length of cover member 552. An outer cross-sectional profile transverse to the longitudinal axis of the cover member 552 can comprise a circle, oval, regular or irregular polygon, square, and/or rectangle shape. The shape or size can vary along the length or width of the cover member 552.

The distal portion of the cover member 552 can comprises an outer surface that rounded or blunt. A round or blunt surface can permit insertion of the cover member through an opening of the patient causing damage to the patient's tissue. The distal portion of the cover member 552 can comprise an outer surface that tapers toward a distal end. The tapered distal portion can permit the cover member 552 to pierce the patient's skin or tissue to allow insertion of the cover member 552.

The cover member 552 comprises cavity 566 that extends between proximal and distal portions of the cover member 552. The passage can extend from the proximal portion toward the distal portion of the cover member 552. The portion of the cover member 552 comprising the cavity can have a cross-sectional profile, transverse to the cover member longitudinal axis, having a circle, oval, regular or irregular polygon, square, and/or rectangle shape. The inner surface of the cover member that forms the cavity can have a profile that corresponds to an outer surface of the piston 554 configured to extend through the cavity. The shape or size of the cavity can vary along the length or width of the cavity. The cavity can permit the piston 554 to extend within the cavity and move along the longitudinal axis of the cover member 552.

The cover member 552 can comprise an elongate aperture 520 configured to permit a portion of the thread 80 to extend into the cavity. The elongate aperture 520 can extend from a location proximal to the distal portion toward the proximal portion of the cover member 552. The elongate aperture 520 can extend along a portion of the cover member 552. The elongate aperture 520 can comprise a length that is approximately equal to the portion of the thread 80 engaged against an inner surface of the cover member 552. For example, in some embodiments, the elongate aperture 520 can comprise a length that is approximately equal to or greater than one-half a length of the thread 80. The elongate aperture 520 can comprise a length that is approximately equal to or greater than three-fourths of a length of the thread 80. In some embodiments, the elongate aperture 520 can comprise a length from about 0.78 inches to about 2.36 inches (about 20 mm to about 60 mm).

The piston 554 can be coupled to the first base 560, and the cover member 552 can be coupled to the second base 562. The piston 554 can extend within the cavity of the cover member 552, from the first base 560 toward the aperture 520 of the cover member 552. The piston 554 comprises a length that corresponds with a length of the cover member cavity. The piston 554 comprises a length that is at least equal to or approximately equal to a length from the proximal portion of the cover member 552 to a distal portion of the elongate aperture 520. The piston 554 length can be approximately equal to or greater than a longitudinal length of the cavity 556.

The distal portion of the piston 554 can comprise an outer surface that tapers toward a distal end. The distal portion of the piston 554 can comprise a tapered distal end surface 564 that is transverse to the longitudinal axis of the piston 554, e.g., a bevel. The tapered distal end surface 564 of the piston 554 can push, eject, or direct a portion of thread 80 from of the cavity 556 when the piston is moved to extend along the elongate aperture 520. The piston 554 can be aligned within the cavity of the cover member 552 so that the tapered surface 564 faces the elongate aperture 520.

In a first configuration, the distal portion of the piston 554 is positioned adjacent to a distal portion of the cover member 552. In the first configuration, the distal portion of the piston 554 can be proximal to the aperture 520, and in some embodiments, may not extend into or fully across the aperture 520.

In the first configuration a portion of the thread 80 can be coupled to the insertion device 550. The proximal portion of the thread 80 can be engaged against the outer surface of the cover member 552, and the distal portion of the thread 80 can extend through the elongate aperture 520 into the cavity. As illustrated in FIG. 25, the distal portion of the thread 80 can be engaged against the inner surface of the cover member 552. The distal portion of the thread 80 can be engaged against an inner surface of the cover member 552 that is opposite the elongate aperture 520. The proximal and/or distal portions of the thread 80 can be adhered to the cover member 552.

In the second configuration, the piston 554 can be moved, relative to the cover member 552, to separate the thread 80 from the insertion device 550. The piston 554 can be moved by urging the distal portion of the first base 560 toward the second base 562. When the first base 560 is moved toward the second base 562, the distal portion of the piston 554 can extend across the portion of the cover member comprising the elongate aperture 520.

The insertion device 550 can be directed toward the patient in the first configuration, so that the distal portion of the cover member 552 is inserted into the skin 90 of the patient. The distal end surface of the cover member 552 can be configured to pierce the skin 90 of the patient to permit movement of the insertion device 550 into the patient.

The insertion device 550 can be moved to the second configuration to separate the thread 80 from the insertion device 550. To separate the thread 80, the distal portion of the piston 554 can be moved toward the aperture 520 of the cover member 552. When the piston 554 moves across the aperture 520, the distal portion of the piston 554 can extend between the inner surface of the cover member 552 and the distal portion of the thread 80. As the piston 554 is moved toward the distal portion of the cover member 552, the distal portion of the thread 80 is separated from the cover member and directed out of the elongate aperture, as illustrated in FIG. 27. Movement of the thread 80 by the piston 554 can cause the proximal portion of the thread 80 to separate from the cover member 552.

To implant the thread 80, the insertion device 550 can be retracted from the thread 80, as illustrated FIG. 28. The insertion device 550 can be retracted until the cover member 552 is withdrawn from the patient. Any portion of the thread 80 that remains extending through the surface of the patient's skin can be separated or cut so that the remaining portion is entirely within the patient's skin.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A thread insertion assembly comprising: a cover member comprising a proximal portion, a distal portion, an inner cavity extending from the proximal portion toward the distal portion, and an aperture through a distal portion of the cover member; a thread comprising a proximal portion and a distal portion, a distal portion of the thread positioned through the aperture; and a piston positioned within the inner cavity, the distal portion of the thread engaged between the piston and the cover member, wherein the thread is released by movement of the piston relative to the cover member.

Clause 2. The thread insertion assembly of Clause 1, wherein the thread is released by proximal retraction of the piston.

Clause 3. The thread insertion assembly of Clause 1, comprising a first base, wherein the piston comprises a proximal portion and a distal portion, the proximal portion coupled to the first base, and the distal portion extending within the inner cavity of the cover member.

Clause 4. The thread insertion assembly of Clause 3, comprising a second base, wherein the proximal portion of the cover member is coupled to the second base, and the first base and piston are moveable relative to the cover member and second base to release the thread.

Clause 5. The thread insertion assembly of Clause 4, wherein the first base comprises a flange extending outwardly relative to the second base.

Clause 6. The thread insertion assembly of Clause 4, wherein a spring is positioned between a proximal portion of the first base and the second base, such that the first base is biased toward the distal portion of the cover member.

Clause 7. The thread insertion assembly of Clause 1, wherein a proximal portion of the thread is engaged against an outer surface of the cover member.

Clause 8. The thread insertion assembly of Clause 7, wherein a fastener retains the proximal portion of the thread against an outer surface of the cover member.

Clause 9. The thread insertion assembly of Clause 1, wherein the aperture extends through a side of the cover member and is transverse to a longitudinal length of the cover member.

Clause 10. The thread insertion assembly of Clause 1, wherein the aperture extends through a distal portion of the cover member.

Clause 11. The thread insertion assembly of Clause 1, wherein the thread is compressed between the piston and cover member in a first configuration and the thread is further compressed between the piston and cover member in a second configuration to release the thread.

Clause 12 The thread insertion assembly of Clause 1, wherein the cover member comprises a hypodermic tube.

Clause 13. The thread insertion assembly of Clause 1, wherein the distal portion of the cover member comprises a bevel (e.g., tri-faceted bevel, single bevel, etc.).

Clause 14. The thread insertion assembly of Clause 1, wherein the cover member comprises a 304 stainless steel or a 316L stainless steel.

Clause 15. A thread insertion assembly comprising: a cover member comprising a proximal portion, a distal portion, an inner cavity extending from the proximal portion toward the distal portion, and an aperture through a distal portion of the cover member; a thread comprising a proximal portion and a distal portion, a distal portion of the thread positioned through the aperture; and a piston positioned within the inner cavity of the cover member, the distal portion of the thread adhered to the piston, wherein the thread is separated from the piston by movement of the piston relative to the cover member.

Clause 16. The thread insertion assembly of Clause 15, wherein the distal portion of the thread is adhered to a distal portion of the piston.

Clause 17. The thread insertion assembly of Clause 15, wherein the distal portion of the thread is crimped by engagement of a portion of the piston against the thread.

Clause 18. The thread insertion assembly of Clause 15, wherein the thread is separated from the piston by proximal retraction of the piston.

Clause 19. The thread insertion assembly of Clause 15, comprising a first base, wherein the piston comprises a proximal portion coupled to the first base, and a distal portion extending within the inner cavity of the cover member.

Clause 20. The thread insertion assembly of Clause 19, comprising a second base, wherein the proximal portion of the cover member is coupled to the second base, and the first base and piston are moveable relative to the cover member and second base to separate the thread.

Clause 21. The thread insertion assembly of Clause 19, wherein a spring is positioned between a proximal portion of the first base and the second base, such that the first base is urged toward the distal portion of the cover member.

Clause 22. The thread insertion assembly of Clause 15, wherein a proximal portion of the thread is engaged against an outer surface of the cover member.

Clause 23. The thread insertion assembly of Clause 22, wherein a fastener retains the proximal portion of the thread against an outer surface of the cover member.

Clause 24. The thread insertion assembly of Clause 15, wherein the cover member comprises a hypodermic tube, and wherein the distal portion of the cover member comprises a bevel.

Clause 25. The thread insertion assembly of Clause 24, wherein the piston comprises a distal end having a beveled surface.

Clause 26. The thread insertion assembly of Clause 25, wherein the piston and the cover member are aligned around respective longitudinal axes such that the bevel of the piston and the cover member align to form a common plane.

Clause 27. The thread insertion assembly of Clause 15, wherein the aperture extends through a side of the cover member and is transverse to a longitudinal length of the cover member.

Clause 28. A thread insertion assembly comprising: a cover member comprising a proximal portion, a distal portion, an inner cavity extending from the proximal portion toward the distal portion, and an aperture through a distal portion of the cover member; a thread comprising a proximal portion and a distal portion, a distal portion of the thread positioned through the aperture and crimped by engagement of the cover member against the thread; and a piston positioned within the inner cavity of the cover member and moveable to contact at least one of the crimped portion of the cover member or the crimped portion of the thread to separate the cover member and the thread, wherein the thread is released from the cover member by movement of the piston.

Clause 29. The thread insertion assembly of Clause 28, comprising a first base, wherein the piston comprises a proximal portion coupled to the first base, and a distal portion extending within the inner cavity of the cover member.

Clause 30. The thread insertion assembly of Clause 29, comprising a second base, wherein the proximal portion of the cover member is coupled to the second base, and the first base and piston are moveable relative to the cover member and second base to release the thread.

Clause 31. The thread insertion assembly of Clause 30, wherein the second base comprises a flange extending outwardly relative to the second base.

Clause 32. The thread insertion assembly of Clause 30, wherein a spring is positioned between a distal portion of the first base and the second base, such that the second base is biased toward the distal portion of the cover member.

Clause 33. The thread insertion assembly of Clause 28, wherein the proximal portion of the thread is engaged against an outer surface of the cover member.

Clause 34. The thread insertion assembly of Clause 33, wherein a fastener retains the proximal portion of the thread against an outer surface of the cover member.

Clause 35. The thread insertion assembly of Clause 28, wherein the thread is crimped by a portion of the cover member proximal to the aperture.

Clause 36. The thread insertion assembly of Clause 28, wherein the aperture extends through a side of the cover member and is transverse to a longitudinal length of the cover member.

Clause 37. The thread insertion assembly of Clause 28, wherein the aperture extends through a distal end portion of the cover member.

Clause 38. A thread insertion assembly comprising: a cover member comprising a proximal portion, a distal portion, an inner cavity extending from the proximal portion toward the distal portion, and an aperture through a distal portion of the cover member; a thread comprising a proximal portion and a distal portion, a distal portion of the thread extending through the aperture; and a piston positioned within the inner cavity of the cover member, wherein distal movement of the piston severs the distal portion of the thread and permits disengagement of the thread from the cover member.

Clause 39. The thread insertion assembly of Clause 38, wherein the distal portion of the thread is adhered to the cover member proximal to the aperture.

Clause 40. The thread insertion assembly of Clause 38, wherein the distal portion of the thread is adhered to the piston.

Clause 41. The thread insertion assembly of Clause 38, wherein the distal portion of the thread is engaged between the piston and the cover member proximal to the aperture.

Clause 42. The thread insertion assembly of Clause 38, comprising a first base, wherein the piston comprises a proximal portion coupled to the first base, and a distal portion extending within the inner cavity of the cover member.

Clause 43. The thread insertion assembly of Clause 42, comprising a second base, wherein the proximal portion of the cover member is coupled to the second base, and the first base and piston are moveable relative to the cover member and second base to disengage the thread.

Clause 44. The thread insertion assembly of Clause 38, wherein the proximal portion of the thread is engaged against an outer surface of the cover member.

Clause 45. The thread insertion assembly of Clause 44, wherein a fastener retains the proximal portion of the thread against an outer surface of the cover member.

Clause 46. The thread insertion assembly of Clause 38, wherein the aperture extends through a side of the cover member and is transverse to a longitudinal length of the cover member.

Clause 47. The thread insertion assembly of Clause 46, wherein the aperture extends through opposing side surfaces of the cover member.

Clause 48. The thread insertion assembly of Clause 47, wherein the distal portion of the thread extends through the aperture between opposing side surfaces of the cover member.

Clause 49. The thread insertion assembly of Clause 46, wherein the piston is engaged against the distal portion of the thread extending through the aperture.

Clause 50. The thread insertion assembly of Clause 38, wherein the cover member comprises a hypodermic tube.

Clause 51. The thread insertion assembly of Clause 38, wherein the distal portion comprises a bevel.

Clause 52. A thread insertion assembly comprising: a cover member comprising a proximal portion, a distal portion, an inner cavity extending from the proximal portion toward the distal portion, and an elongate aperture through the cover member and extending from a location proximal to the distal portion toward the proximal portion; a thread comprising a proximal portion and a distal portion, a distal portion of the thread positioned within the inner cavity of the cover member, and the proximal portion extending along an outer surface of the cover member; a piston positioned within the inner cavity of the cover member, wherein distal advancement of the piston displaces the thread through the elongate aperture.

Clause 53. The thread insertion assembly of Clause 52, wherein the distal portion of the thread is coupled to the cover member proximal to the aperture.

Clause 54. The thread insertion assembly of Clause 52, wherein the distal portion of the thread is adhered to the cover member proximal to the aperture.

Clause 55. The thread insertion assembly of Clause 52, wherein the proximal portion of the thread is adhered to the outer surface of the cover member.

Clause 56. The thread insertion assembly of Clause 52, comprising a first base, wherein the piston comprises a proximal portion coupled to the first base, and a distal portion extending within the inner cavity of the cover member.

Clause 57. The thread insertion assembly of Clause 56, comprising a second base, wherein the proximal portion of the cover member is coupled to the second base, and the first base and piston are moveable relative to the cover member and second base to displace the thread.

Clause 58. The thread insertion assembly of Clause 52, wherein a length of the aperture is from about 0.78 inches to about 2.36 inches (about 20 mm to about 60 mm).

Clause 59. The thread insertion assembly of Clause 52, wherein a length of the aperture is approximately three-fourths of a length of the thread.

Clause 60. The thread insertion assembly of Clause 52, wherein a length of the piston is from about 0.78 inches to about 3.15 inches.

Clause 61. The thread insertion assembly of Clause 52, wherein a length of the piston is approximately equal to the length of the inner cavity.

Clause 62. A method of inserting a thread comprising: inserting a distal portion of a cover member into a patient, wherein the cover member comprises a proximal portion, a distal portion, an inner cavity extending from the proximal portion toward the distal portion of the cover member, and an aperture extending through the distal portion of the cover member; moving a piston, positioned within the inner cavity and extending from the proximal portion toward the distal portion of the cover member, relative to the cover member to separate a distal portion of a thread positioned through the aperture; and retracting the distal portion of the cover member from the patient.

Clause 63. The method of Clause 62, comprising removing a fastener to release a proximal portion of the thread against an outer surface of the cover member.

Clause 64. The method of Clause 62, comprising piercing a patient with a distal portion of the cover member.

Clause 65. The method of Clause 62, wherein decoupling the distal portion of the thread comprises moving a first base, coupled to a proximal portion of the piston, relative to a second base, coupled to the proximal portion of the cover member.

Clause 66. The method of Clause 62, wherein decoupling the distal portion of the thread comprises retracting the piston proximally to the distal portion of the cover member to release the distal portion of the thread positioned through the aperture.

Clause 67. The method of Clause 62, wherein decoupling the distal portion of the thread comprises advancing the piston toward the distal portion of the cover member to separate a distal portion of a thread coupled to the cover member.

Clause 68. The method of Clause 62, wherein decoupling the distal portion of the thread comprises advancing the piston toward the distal portion of the cover member to separate a crimped a portion of the cover member.

Clause 69. The method of Clause 62, wherein decoupling the distal portion of the thread comprises moving the piston to cut the thread.

Clause 70. A method of inserting a thread comprising: inserting a distal portion of a cover member into a patient, wherein the cover member comprises a proximal portion of the cover member, a distal portion, an inner cavity extending from the proximal portion toward a distal portion, and an aperture extending through a distal portion of the cover member; moving a piston, positioned within the inner cavity and extending from the proximal portion toward the distal portion of the cover member, relative to the cover member to separate a distal portion of a thread positioned through the aperture and coupled to the piston; and retracting the distal portion of the cover member from the patient.

Clause 71. The method of Clause 70, wherein decoupling the distal portion of the thread comprises moving a first base, coupled to a proximal portion of the piston, relative to a second base, coupled to a proximal portion of the cover member.

Clause 72. The method of Clause 70, wherein decoupling the distal portion of the thread comprises retracting the piston proximally to the distal portion of the cover member to separate the distal portion of the thread positioned through the aperture.

Clause 73, A method of inserting a thread comprising: inserting a distal portion of a cover member into a patient, wherein the cover member comprises a proximal portion of the cover member, a distal portion, an inner cavity extending from the proximal portion toward a distal portion, and an elongate aperture through the cover member and extending from a location proximal to the distal portion toward the proximal portion; moving a piston, positioned within the inner cavity and extending from the proximal portion toward the distal portion of the cover member, relative to the cover member to displace a distal portion of a thread positioned within the inner cavity through the aperture; and retracting the piston and the distal portion of the cover member from the patient.

Clause 74. The method of Clause 73, wherein displacing the distal portion of the thread comprises moving a first base, coupled to a proximal portion of the piston, relative to a second base, coupled to a proximal portion of the cover member.

Clause 75. The method of Clause 73, wherein displacing the distal portion of the thread comprises advancing the piston toward the distal portion of the cover member to move the distal portion of the thread through the aperture.

Clause 76. The method of Clause 73, wherein displacing the distal portion of the thread comprises advancing a distal portion of the piston along a longitudinal length of the thread, between the thread and the cover member, to move the distal portion of the thread through the aperture.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only; do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A thread insertion assembly comprising:
   a first base comprising first and second arms;
   a second base comprising a sidewall forming an inner cavity and a channel that extends from the cavity through the sidewall, wherein the first base is positioned within the cavity with the first and second arms extending through the channel;
   a cover member comprising a proximal portion, a distal portion, an inner cavity extending from the proximal portion toward the distal portion of the cover member, and an aperture through the distal portion of the cover member, wherein the proximal portion of the cover member is coupled to the second base;
   a thread comprising a proximal portion and a distal portion, the distal portion of the thread positioned through the aperture; and
   a piston comprising a proximal portion and a distal portion, the proximal portion of the piston coupled to the first base, and the distal portion of the piston is positioned within the inner cavity, the distal portion of the thread engaged between the piston and the cover member, wherein the thread is released by movement of the first and second arms relative to the second base.

2. The thread insertion assembly of claim 1, wherein the thread is released by proximal retraction of the piston.

3. The thread insertion assembly of claim 1, wherein a spring is positioned between a proximal portion of the first base and the second base, such that the first base is biased toward the distal portion of the cover member.

4. The thread insertion assembly of claim 1, wherein a proximal portion of the thread is engaged against an outer surface of the cover member.

5. The thread insertion assembly of claim 1, wherein the aperture extends through a side of the cover member and is transverse to a longitudinal length of the cover member.

6. The thread insertion assembly of claim 4, wherein a fastener retains the proximal portion of the thread against an outer surface of the cover member.

7. The thread insertion assembly of claim 1, wherein the thread is released by proximal retraction of the first and second arms.

8. The thread insertion assembly of claim 1, wherein the aperture extends through a side of the cover member and is transverse to a longitudinal length of the cover member.

9. The thread insertion assembly of claim 1, wherein the cover member comprises a hypodermic tube.

10. The thread insertion assembly of claim 1, wherein the distal portion of the cover member comprises a bevel outer surface.

11. The thread insertion assembly of claim 1, wherein the cover member comprises a stainless steel.

\* \* \* \* \*